(12) United States Patent
Ben David et al.

(10) Patent No.: US 8,386,056 B2
(45) Date of Patent: Feb. 26, 2013

(54) PARASYMPATHETIC STIMULATION FOR TREATING ATRIAL ARRHYTHMIA AND HEART FAILURE

(75) Inventors: Tamir Ben David, Tel Aviv (IL); Shai Ayal, Jerusalem (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1509 days.

(21) Appl. No.: 11/070,842

(22) Filed: Feb. 24, 2005

(65) Prior Publication Data

US 2005/0187586 A1    Aug. 25, 2005

Related U.S. Application Data

(63) Continuation of application No. 10/719,659, filed on Nov. 20, 2003, now Pat. No. 7,778,711, which is a continuation-in-part of application No. PCT/IL03/00431, filed on May 23, 2003, which is a continuation-in-part of application No. 10/205,475, (Continued)

(51) Int. Cl.
*A61N 1/00* (2006.01)
(52) U.S. Cl. ....................................... 607/118
(58) Field of Classification Search ................... 607/5, 9, 607/14, 62, 118
See application file for complete search history.

(56) References Cited

U.S. PATENT DOCUMENTS

| | | | |
|---|---|---|---|
| 3,411,507 A | 11/1968 | Wingrove | |
| 4,019,518 A | 4/1977 | Maurer et al. | |
| 4,161,952 A | 7/1979 | Kinney et al. | |
| 4,338,945 A | 7/1982 | Kosugi et al. | |
| 4,392,496 A | 7/1983 | Stanton | |
| 4,535,785 A | 8/1985 | van den Honert | |
| 4,559,948 A | 12/1985 | Liss et al. | |
| 4,573,481 A | 3/1986 | Bullara | |
| 4,585,005 A | 4/1986 | Lue et al. | |
| 4,602,624 A | 7/1986 | Naples | |
| 4,608,985 A | 9/1986 | Crish | |
| 4,628,942 A | 12/1986 | Sweeney | |
| 4,632,116 A | 12/1986 | Rosen | |
| 4,649,936 A | 3/1987 | Ungar | |
| 4,663,102 A | 5/1987 | Brenman et al. | |
| 4,702,254 A | 10/1987 | Zabara | |

(Continued)

FOREIGN PATENT DOCUMENTS

| EP | 0 688 577 A1 | 12/1995 |
|---|---|---|
| EP | 0831954 | 4/1998 |

(Continued)

OTHER PUBLICATIONS

Chiou, C.W., et al., "Efferent vagal innervation of the canine atria and sinus and atrioventricular nodes", Circulation, 1997, vol. 95, p. 2573.

(Continued)

*Primary Examiner* — Mark W Bockelman
(74) *Attorney, Agent, or Firm* — Sughrue Mion, PLLC

(57) ABSTRACT

Apparatus is provided that includes an electrode device, adapted to be coupled to a vagus nerve of a subject, and a control unit, adapted to drive the electrode device to apply to the vagus nerve a current that reduces heart rate variability of the subject. Also provided is a method comprising applying to a vagus nerve of a subject a current that reduces heart rate variability of the subject.

6 Claims, 6 Drawing Sheets

Related U.S. Application Data filed on Jul. 24, 2002, now Pat. No. 7,778,703, which is a continuation-in-part of application No. PCT/IL02/00068, filed on Jan. 23, 2002, which is a continuation-in-part of application No. 09/944,913, filed on Aug. 31, 2001, now Pat. No. 6,684,105.

(60) Provisional application No. 60/383,157, filed on May 23, 2002.

(56) References Cited

U.S. PATENT DOCUMENTS

| | | | |
|---|---|---|---|
| 4,739,764 A | 4/1988 | Lue | |
| 4,867,164 A | 9/1989 | Zabara | |
| 4,926,865 A | 5/1990 | Oman | |
| 4,962,751 A | 10/1990 | Krauter | |
| 5,025,807 A | 6/1991 | Zabara | |
| 5,042,497 A | 8/1991 | Shapland | |
| 5,058,599 A | 10/1991 | Andersen et al. | |
| 5,069,680 A | 12/1991 | Grandjean | |
| 5,139,020 A | 8/1992 | Koestner et al. | |
| 5,170,802 A | 12/1992 | Mehra | |
| 5,178,161 A | 1/1993 | Kovacs | |
| 5,188,104 A | 2/1993 | Wernicke | |
| 5,199,428 A | 4/1993 | Obel et al. | |
| 5,199,430 A | 4/1993 | Fang | |
| 5,203,326 A * | 4/1993 | Collins | 607/4 |
| 5,205,285 A | 4/1993 | Baker, Jr. | |
| 5,215,086 A | 6/1993 | Terry, Jr. | |
| 5,224,491 A | 7/1993 | Mehra | |
| 5,243,980 A | 9/1993 | Mehra | |
| 5,263,480 A | 11/1993 | Wernicke | |
| 5,282,468 A | 2/1994 | Klepinski | |
| 5,292,344 A | 3/1994 | Douglas | |
| 5,299,569 A | 4/1994 | Wernicke | |
| 5,314,495 A | 5/1994 | Kovacs | |
| 5,330,507 A | 7/1994 | Schwartz | |
| 5,334,221 A | 8/1994 | Bardy | |
| 5,335,657 A | 8/1994 | Terry, Jr. | |
| 5,356,425 A | 10/1994 | Bardy | |
| 5,411,531 A | 5/1995 | Hill et al. | |
| 5,423,872 A | 6/1995 | Cigaina | |
| 5,437,285 A | 8/1995 | Verrier et al. | |
| 5,439,938 A | 8/1995 | Snyder et al. | |
| 5,454,840 A | 10/1995 | Krakovsky et al. | |
| 5,507,784 A | 4/1996 | Hill et al. | |
| 5,522,854 A | 6/1996 | Ideker et al. | |
| 5,540,730 A | 7/1996 | Terry, Jr. | |
| 5,540,734 A | 7/1996 | Zabara | |
| 5,562,718 A | 10/1996 | Palermo | |
| 5,571,150 A | 11/1996 | Wernicke | |
| 5,578,061 A | 11/1996 | Stroetmann et al. | |
| 5,615,684 A | 4/1997 | Hagel et al. | |
| 5,634,462 A | 6/1997 | Tyler | |
| 5,645,570 A * | 7/1997 | Corbucci | 607/5 |
| 5,658,318 A * | 8/1997 | Stroetmann et al. | 607/6 |
| 5,690,681 A | 11/1997 | Geddes et al. | |
| 5,690,691 A | 11/1997 | Chen | |
| 5,700,282 A | 12/1997 | Zabara | |
| 5,707,400 A | 1/1998 | Terry, Jr. | |
| 5,711,316 A | 1/1998 | Elsberry et al. | |
| 5,716,385 A | 2/1998 | Mittal | |
| 5,749,900 A * | 5/1998 | Schroeppel et al. | 607/4 |
| 5,755,750 A | 5/1998 | Petruska | |
| 5,824,027 A | 10/1998 | Hoffer | |
| 5,832,932 A | 11/1998 | Elsberry et al. | |
| 5,833,709 A | 11/1998 | Rise et al. | |
| 5,836,994 A | 11/1998 | Bourgeois | |
| 5,916,239 A * | 6/1999 | Geddes et al. | 607/14 |
| 5,938,584 A | 8/1999 | Ardito et al. | |
| 6,006,134 A | 12/1999 | Hill et al. | |
| 6,026,326 A | 2/2000 | Bardy | |
| 6,038,476 A | 3/2000 | Schwartz | |
| 6,058,328 A | 5/2000 | Levine et al. | |
| 6,058,331 A | 5/2000 | King et al. | |
| 6,066,163 A | 5/2000 | John | |
| 6,073,048 A | 6/2000 | Kieval et al. | |
| 6,083,249 A | 7/2000 | Familoni | |
| 6,086,525 A | 7/2000 | Davey et al. | |
| 6,091,922 A | 7/2000 | Bisaiji | |
| 6,091,977 A | 7/2000 | Tarjan et al. | |
| 6,094,598 A | 7/2000 | Elsberry et al. | |
| 6,097,984 A | 8/2000 | Douglas | |
| 6,104,955 A | 8/2000 | Bourgeois | |
| 6,104,956 A | 8/2000 | Naritoku et al. | |
| 6,104,960 A | 8/2000 | Duysens et al. | |
| 6,119,516 A | 9/2000 | Hock | |
| 6,134,470 A | 10/2000 | Hartlaub | |
| 6,146,335 A | 11/2000 | Gozani | |
| 6,161,029 A | 12/2000 | Spreigl et al. | |
| 6,167,304 A | 12/2000 | Loos | |
| 6,169,924 B1 | 1/2001 | Meloy et al. | |
| 6,195,584 B1 | 2/2001 | Hill et al. | |
| 6,205,359 B1 | 3/2001 | Boveja | |
| 6,230,061 B1 | 5/2001 | Hartung | |
| 6,240,314 B1 | 5/2001 | Plicchi et al. | |
| 6,266,564 B1 | 7/2001 | Hill et al. | |
| 6,272,377 B1 | 8/2001 | Sweeney et al. | |
| 6,292,695 B1 | 9/2001 | Webster, Jr. et al. | |
| 6,319,241 B1 | 11/2001 | King | |
| 6,341,236 B1 | 1/2002 | Osorio | |
| 6,356,784 B1 | 3/2002 | Lozano et al. | |
| 6,366,813 B1 | 4/2002 | DiLorenzo | |
| 6,381,499 B1 | 4/2002 | Taylor et al. | |
| 6,400,982 B2 | 6/2002 | Sweeney et al. | |
| 6,405,079 B1 | 6/2002 | Ansarinia | |
| 6,434,424 B1 | 8/2002 | Igel et al. | |
| 6,449,507 B1 | 9/2002 | Hill et al. | |
| 6,463,328 B1 | 10/2002 | John | |
| 6,473,644 B1 | 10/2002 | Terry et al. | |
| 6,493,585 B2 | 12/2002 | Plicchi et al. | |
| 6,511,500 B1 | 1/2003 | Rahme | |
| 6,522,926 B1 | 2/2003 | Kieval et al. | |
| 6,542,774 B2 | 4/2003 | Hill et al. | |
| 6,564,096 B2 | 5/2003 | Mest | |
| 6,571,122 B2 | 5/2003 | Schroeppel et al. | |
| 6,587,727 B2 | 7/2003 | Osorio et al. | |
| 6,600,956 B2 | 7/2003 | Maschino | |
| 6,610,713 B2 | 8/2003 | Tracey | |
| 6,622,041 B2 | 9/2003 | Terry, Jr. et al. | |
| 6,628,987 B1 | 9/2003 | Hill et al. | |
| 6,668,191 B1 | 12/2003 | Boveja | |
| 6,671,556 B2 | 12/2003 | Osorio et al. | |
| 6,684,105 B2 * | 1/2004 | Cohen et al. | 607/63 |
| 6,690,971 B2 | 2/2004 | Schauerte et al. | |
| 6,694,186 B2 | 2/2004 | Bardy | |
| RE38,705 E | 2/2005 | Hill et al. | |
| 6,865,416 B2 | 3/2005 | Dev et al. | |
| 6,885,888 B2 | 4/2005 | Rezai | |
| 6,895,280 B2 | 5/2005 | Meadows et al. | |
| 6,907,293 B2 | 6/2005 | Grill et al. | |
| 6,907,295 B2 | 6/2005 | Gross et al. | |
| 6,928,320 B2 | 8/2005 | King | |
| 6,934,583 B2 | 8/2005 | Weinberg et al. | |
| 6,985,774 B2 | 1/2006 | Kieval et al. | |
| 7,050,846 B2 | 5/2006 | Sweeney et al. | |
| 7,076,299 B2 | 7/2006 | Thong | |
| 7,136,700 B1 | 11/2006 | Province | |
| 7,142,917 B2 | 11/2006 | Fukui | |
| 7,403,819 B1 | 7/2008 | Shelchuk et al. | |
| 7,738,952 B2 | 6/2010 | Yun et al. | |
| 7,778,703 B2 | 8/2010 | Gross et al. | |
| 7,778,711 B2 | 8/2010 | Ben-David et al. | |
| 2002/0035335 A1 | 3/2002 | Schauerte | |
| 2002/0107553 A1 | 8/2002 | Hill et al. | |
| 2002/0120304 A1 | 8/2002 | Mest | |
| 2002/0156004 A1 | 10/2002 | Baker et al. | |
| 2003/0018367 A1 | 1/2003 | DiLorenzo | |
| 2003/0027794 A1 | 2/2003 | Arnaiz et al. | |
| 2003/0040774 A1 | 2/2003 | Terry et al. | |
| 2003/0045909 A1 | 3/2003 | Gross et al. | |
| 2003/0045914 A1 | 3/2003 | Cohen et al. | |
| 2003/0050677 A1 | 3/2003 | Gross et al. | |
| 2003/0078623 A1 | 4/2003 | Weinberg et al. | |

| | | | |
|---|---|---|---|
| 2003/0100924 | A1 | 5/2003 | Foreman et al. |
| 2003/0195574 | A1 | 10/2003 | Osorio et al. |
| 2003/0216775 | A1 | 11/2003 | Hill et al. |
| 2003/0216792 | A1 | 11/2003 | Levin et al. |
| 2003/0229380 | A1 | 12/2003 | Adams et al. |
| 2003/0233129 | A1 | 12/2003 | Matos |
| 2003/0236558 | A1 | 12/2003 | Whitehurst et al. |
| 2004/0015205 | A1 | 1/2004 | Whitehurst et al. |
| 2004/0048795 | A1 | 3/2004 | Ivanova et al. |
| 2004/0059392 | A1 | 3/2004 | Parramon et al. |
| 2004/0138721 | A1 | 7/2004 | Osorio et al. |
| 2004/0152958 | A1 | 8/2004 | Frei et al. |
| 2004/0158119 | A1 | 8/2004 | Osorio et al. |
| 2004/0162594 | A1 | 8/2004 | King |
| 2004/0172075 | A1 | 9/2004 | Shafer et al. |
| 2004/0199210 | A1 | 10/2004 | Shelchuk |
| 2004/0215289 | A1 | 10/2004 | Fukui |
| 2004/0243182 | A1 | 12/2004 | Cohen et al. |
| 2004/0249416 | A1 | 12/2004 | Yun et al. |
| 2004/0254612 | A1 | 12/2004 | Ben-Ezra et al. |
| 2005/0131467 | A1 | 6/2005 | Boveja |
| 2005/0187584 | A1 | 8/2005 | Denker et al. |
| 2005/0222644 | A1 | 10/2005 | Killian et al. |
| 2006/0015153 | A1 | 1/2006 | Gliner et al. |
| 2006/0047325 | A1 | 3/2006 | Thimineur et al. |
| 2006/0052831 | A1 | 3/2006 | Fukui |
| 2006/0064140 | A1 | 3/2006 | Whitehurst et al. |
| 2006/0074450 | A1 | 4/2006 | Boveja et al. |
| 2006/0129205 | A1 | 6/2006 | Boveja et al. |
| 2006/0149337 | A1 | 7/2006 | John |
| 2006/0167498 | A1 | 7/2006 | DiLorenzo |

FOREIGN PATENT DOCUMENTS

| | | |
|---|---|---|
| WO | WO-01/10375 A2 | 2/2001 |
| WO | WO-01-10432 | 2/2001 |
| WO | WO 01/26729 | 4/2001 |
| WO | WO 02/085448 A1 | 10/2002 |
| WO | WO 03/018113 A1 | 3/2003 |
| WO | WO 03/099377 A1 | 12/2003 |
| WO | WO-2006/102370 A2 | 9/2006 |

OTHER PUBLICATIONS

Cummings, J.E., et al., "Preservation of the anterior fat pad paradoxically decreases the incidence of postoperative atrial fibrillation in humans", J. Am. Coll. Cardiol., 2001, vol. 43, No. 6, pp. 994-1000.
Fitzpatrick, et al. "A Nerve Cuff Design for the Selective Activation and Blocking of Myelinated Nerve Fibres", Annual Conference of the IEEE Engineering in Medicine and Biology Society, vol. 13, No. 2, 1991.
Kwan, Herman, et al., "Cardiovascular adverse drug reactions druing initiation of antiarrhythmic therapy for atrial fibrillation", Can. J. Hosp. Pharm., 2001, vol. 54, pp. 10-14.
Baratta, et al. "Orderly stimulation of Skeletal Muscle Motor Units with Tripolar Nerve Cuff Electrode", IEEE Transactions of Biomedical Engineering, vol. 36, No. 8, Aug. 1989, pp. 836-843.
Hjalmarson, Ake, "Prevention of sudden cardiac death with beta blockers", Clin. Cardiol., 1999, vol. 22, Supoplement V, pp. V-11-V-15.
Cortese, J.F. "Vagus Nerve Stimulation for Control of Intractable Epileptic Seizures" available at http://www.science.wayne.edu/~bio340/StudentPages/corese/, May 31, 2001.
Bilgutay, Aydin M., et al., "Vagal tuning a new concept in the treatment of supraventricular arrhythmias, angina pectoris and heart failure", J. Thoracic Cardiovasc. Surg., vol. 56, No. 1, pp. 71-82, Jul. 1968.
Manfredi, M., "Differentiating Blocks of conduction of larger fibers in peripheral nerve by direct current", Arch. Ital. Biol., vol. 108, pp. 52-71, 1970.
M. Hirose, "Pituitary adenylate cyclase-activating polypeptide-27 causes a biphasic chronotropic effect and atrial fibrillation in autonomically decentralized, anesthetized dogs", The Journal of Pharmacology and Experimental Therapeutics, vol. 283, No. 2, pp. 478-487, 1997.
Devor, M. "Pain Networks", Handbook of Brand Theory and Neural Networks, Ed. M.A. Arbib, MIT Press, p. 698, 1998.
Patent Abstracts of Japan; vol. 1998, No. 09, Jul. 31, 1998 & JP 10 096577 A (Matsushita Refrig Co Ltd), Apr. 14, 1998.
Friedrichs, Gregory S., "Experimental models of atrial fibrillation/flutter", Journal of Pharmacological and Toxoligical Methods, 2000, vol. 43, pp. 117-1123.
Wallick, et al., "Selective AV nodal vagal stimulation improves hemodynamics during acute atrial fibrillation in dogs", Am J. Physiol Heart Circ Physiol, 281: H1490-H1497, 2001.
Rijkhoff, N.J.M., et al. "Orderly recruitment of motoneurons in an acute rabbit model", 20th Annual International Conference of the IEEE Engineering in Medicine and Biology Society, vol. 20, No. 5, 1998, pp. 2564-2565.
Rijkhoff, N.J.M., et al., "Selective Stimulation of Small Diameter Nerve Fibers in a Mixed Bundle", Proceedings of the Annual Project Meeting Sensations/Neuros and Mid Term Review Meeting Neuros, pp. 21-23, Apr. 1999.
Sweeney, James D., et al. "A Nerve Cuff Technique for Selective Excitation of Peripheral Nerve Trunk Regions", IEEE Transactions on Biomedical Engineering, vol. 37, No. 7, Jul. 1990.
Van Den Honert, et al. "A Technique for Collision Block of Peripheral Nerve: Frequency Dependence", IEEE Transactions of Biomedical Engineering, vol. BME-28, No. 5, May 1981, pp. 379-382.
Van Den Honert, et al. "Generation of Unidirectionally Propagated Action Potentials in a Peripheral Nerve by Brief Stimuli", Science magazine, vol. 206, Dec. 14, 1979, pp. 1311-1312.
Zhang, Y., et al., "Optimal Ventricular Rate Slowing During Atrial Fibrillation by Feedback AV Nodal-Selective Vagal Stimulation", Am. J. Physiol. Heart Circ. Physiol. 282:H1102-H1110, 2002.
Schauerte, et al, "Catheter stimulation of cariac parasympathetic nerves in humans", available at http://www.circulationaha.org, pp. 2430-2435, 2001.
Fuster, Valentin, et al., "ACC/AHA/ESC Practice Guidelines", JACC, vol. 38, No. 4, 2001.
Naples, Gregory G., et al. "A Spiral Nerve Cuff Electrode for Peripheral Nerve Stimulation", IEEE Transactions of Biomedical Engineering, vol. 35, No. 11, Nov. 1998, pp. 905-916.
Sweeney, James D., et al. "An Asymmetric Two Electrode Cuff for Generation of Unidirectionally Propagated Action Potentials", IEEE Transactions on Biomedical Engineering, vol. BME-33, No. 6, Jun. 1986.
Website: http://www.bcm.tmc.edu/neurol/struct/epilep/epilipsy_vagus.html, May 31, 2001.
Tsuboi et al., "Inotropic, chronotropic and dromotropic effects mediated via parasympathetic ganglia in the dog heart", Am J. Physiol Heart Circ Physiol, 279: H1201-H1207, 2000.
Ungar, I. J., et al. "Generation of Unidirectionally Propagating Action Potentials Using a Monopolar Electrode Cuff", Annals of Biomedical Engineering, vol. 14, pp. 437-450, 1986.
U.S. Appl. No. 09/824,682 entitled "Method and Apparatus for Selective Control of Nerve Fibers" filed Apr. 4, 2001.
Jideus, "Atrial fibrillation after corony artery bypass surgery", Acta Universitatis Upsaliensis, Uppsala 2001.
Li et al., "Promotion of atrial fibrillation by heart failure in dogs", Circulation, Jul. 6, 1999, pp. 87-95.
U.S. Appl. No. 60/263,834, entitled "Selective Blocking of Nerve Fibers", filed Jan. 25, 2001.
Zhang, et al., "Optimal vertricular rate slowing during atrial fibrillation by feedback AV nodal-selective vagal stimulation", Am J. Physiol Heart Circ Physiol 282:H1102-H1110, 2002.
Rijkhoff et al., "Selective Stimulation of Small Diameter Nerve Fibers in a Mixed Bundle", Proceedings of the Annual Project Meeting Sensations/Neurons and Mid Term Review Meeting Neuros, 21-23, Apr. 1999.
Manfredi, "Differential Block of Conduction of larger fibers in peripheral nerve by direct current", Arch. Ital. Biol. 108:52-71, 1970.
Schaldach M, "New concepts in electrotherapy of the heart", Electrotherapy of the Heart, Springer Verlag Heidelberg, pp. 210-214 (1992).
Nov. 1, 2007 Office Action, issued by the U.S. Patent and Trademark Office, in connection with U.S. Appl. No. 10/205,475.
Apr. 5, 2007 Office Action, issued by the U.S. Patent and Trademark Office, in connection with U.S. Appl. No. 10/488,334.

Apr. 25, 2007 Office Action, issued by the U.S. Patent and Trademark Office, in connection with U.S. Appl. No. 10/488,334.

Jones, et al., (1995) "Heart Rate Responses to Selective Stimulation of Cardiac Vagal C Fibres in Anaesthetized Cats, Rats, and Rabbits," *Journal of Physiology*, 489.1: 203-214.

Jones, et al., (1998) "Activity of C Fibre Cardiac Vagal Efferents in Anaesthetized Cats and Rats," *Journal of Physiology*, 507.3: 869-880.

Furukawa Y et al., "Differential blocking effects of atropine and gallamine on negative chrontropic and dromotropic responses to vagus stimulation in anesthetized dogs," J Pharmacol Exp. Ther. 251(3):797-802 (1989).

Bluemel KM, "Parasympathetic postganglionic pathways to the sinoatrial node, " J Physiol. 259 (5 Pt 2): H1504-10 (1990).

Mazqalev TN, "AV Nodal Physiology," Heart Rhythm Society (www.hrsonline.org), no date.

Bibevski S et al. "Ganglionic Mechanisms Contribute to Diminished Vagal Control in Heart Failure," Circulation 99:2958-2963 (1999).

Garrigue S et al., "Post-ganglionic vagal stimulation of the atrioventricular node reduces ventricular rate during atrial fibrillation, "Pace 21(4), Part II, 878 (1998).

Chen SA et al., "Intracardiac stimulation of human parasympathetic nerve fibers induces negative dromotropic effects: implication with the lesions of radiofrequency catheter ablation, " J Cardiovasc Electrophysiol. 9(3):245-52 (1998).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Waninger MS et al., "Electrophysiological control of ventricular rate during atrial fibrillation," PACE 23:1239-1244 (2000).

Goldberger JJ et al., "New technique for vagal nerve stimulation," J Neurosci Methods. 91(1-2):1089-14 (1999).

Carlson MD et al., "Selective stimulation of parasympathetic nerve fibers to the human sinoatrial node," Circulation 85:1311-1317 (1992).

Pagé PL et al., "Regional distribution of atrial electrical changes induced by stimulation of extracardiac and intracardia neural elements," J. Thorac Cardiovasc Surg. 109(2):377-388 (1995).

Office Adtion, issued Jun. 24, 2009, in connection with U.S. Appl. No. 11/978,379, filed Oct. 29, 2007.

Office Action, issued Aug. 6, 2009, in connection with U.S. Appl. No. 10/205,475, filed Jul. 24, 2002.

Office Action, issued Aug. 21, 2009, in connection with U.S. Appl. No. 11/975,169, filed Oct. 17, 2007.

Office Action, issued Aug. 21, 2009, in connection with U.S. Appl. No. 11/975,240, filed Oct. 17, 2007.

Office Action, issued Aug. 25, 2009, in connection with U.S. Appl. No. 11/975,241, filed Oct. 17, 2007.

Office Action, issued Nov. 9, 2009, in connection with U.S. Appl. No. 11/064,446, filed Feb. 22, 2005.

Morillo et al. (Mar. 1995). Chronic rapid atrial pacing. Structural, functional, and electrophysiological characteristics of a new model of sustained atrial fibrillation. *Circulation*, 91(5), 1588-95.

Office Action, issued Feb. 5, 2010, in connection with U.S. Appl. No. 11/974,951, filed Oct. 16, 2007.

Office Action, issued Feb. 24, 2010, in connection with U.S. Appl. No. 10/866,601, filed Jun. 10, 2004.

Office Action, issued Feb. 24, 2010, in connection with U.S. Appl. No. 11/234,877, filed Sep. 22, 2005.

Office Action, issued Feb. 24, 2010, in connection with U.S. Appl. No. 11/359,266, filed Feb. 21, 2006.

Office Action, issued Mar. 15, 2010, in connection with U.S. Appl. No. 11/724,899, filed Mar. 16, 2007.

U.S. Appl. No. 60/383,157, filed May 23, 2002, Ayal et al.

Office Action, issued Apr. 6, 2010, in connection with U.S. Appl. No. 11/977,291, filed Oct. 23, 2007.

Office Action, issued Jun. 23, 2010, in connection with U.S. Appl. No. 11/978,379, filed Oct. 29, 2007.

Office Action, issued Jun. 29, 2010, in connection with U.S. Appl. No. 11/064,446, filed Feb. 22, 2005.

Office Action, issued Jul. 8, 2010, in connection with U.S. Appl. No. 11/657,784, filed Jan. 24, 2007.

Office Action, issued Jul. 9, 2010, in connection with U.S. Appl. No. 11/977,646, filed Oct. 24, 2007.

Office Action, issued Oct. 12, 2010, in connection with U.S. Appl. No. 11/974,951, filed Oct. 16, 2007.

Office Action, issued Oct. 27, 2010, in connection with U.S. Appl. No. 11/977,291, filed Oct. 23, 2007.

Office Action issued Jun. 27, 2008 during the prosecution of U.S. Appl. No. 10/205,475.

Akselrod, S. et al., (1981) "Power spectrum analysis of heart rate fluctuation: A quantitative probe of beat-to-beat cardiovascular control," *Science* vol. 213: 220-222.

Billette, J. et al., (1975) "Roles of the AV junction in determining the ventricular response to atrial fibrillation," *Canadian Journal of Physiological Pharmacology* 53(4)575-585.

Borovikova, L. et al., (May 25, 2000) "Vagus nerve stimulation attenuates the systemic inflammatory response to endotoxin," *Nature* 405:458-62.

De Ferrari, G., (1991)"Vagal reflexes and survival during acute myocardial ischemia in conscious dogs with healed myocardial infarction," *American Journal of Physiology* 261(1 Pt 2):H63-69.

Deurloo, K. et al., (1998) "Transverse tripolar stimulation of peripheral nerve: a modeling study of spatial selectivity," *Medical & Biological Engineering & Computing*, 36(1):66-74.

Fang, Zi-Ping and Mortimer, J. Thomas, (1991) "Selective activation of small motor axons by quasitrapezoidal current pulses," *IEEE Transactions on Biomedical Engineering*, 38(2):168-174.

Feliciano, L. et al., (1998) "Vagal nerve stimulation releases vasoactive intestinal peptide which significantly increases coronary artery blood flow," *Cardiovascular Research* vol. 40:45-55.

Goodall, E et al., (1996) "Position-selective activation of peripheral nerve fibers with a cuff electrode," *IEEE Transactions on Biomedical Engineering*, 43 (8):851-856.

Grill, W., (1997) "Inversion of the current-distance relationship by transient depolarization," *IEEE Transactions on Biomedical Engineering*, 44(1):1-9.

Higgins, C. et al., S. (1973) "Parasympathetic control of the heart," Pharmacological. *Reviews* 25(1):120-155.

Iwao, T. et al., (2000) "Effect of constant and intermittent vagal stimulation on the heart rate and heart rate variability in rabbits," *Japanese Journal of Physiology* 50:33-39.

Jones, J. et al., (1998) "Activity of C fibre cardiac vagal efferents in anaesthetized cats and rats", *Journal of Physiology*, 507(3):869-880.

Jones, J. et al., (1995) "Heart rate responses to selective stimulation of cardiac vagal C fibres in anaesthetized cats, rats and rabbits", *Journal of Physiology*, 489(1):203-214.

Kamath, M. et al., (1992) "Effect of vagal nerve electrostimulation on the power spectrum of heart rate variability in man," PACE vol. 15, *Clinical Electrophysiology*, vol. 15:235-243.

Levy, M. and Blattberg, B., (Feb. 1976) "Effect of vagal stimulation on the overflow of norepinephrine into the coronary sinus during sympathetic nerve stimulation in the dog," *Circulation Research* 38(2):81-85.

Martin, P. et al., (1983) "Phasic effects of repetitive vagal stimulation on atrial contraction," *Circulation Research* 52(6):657-663.

Morady, F. et al., (1990) "Effects of resting vagal tone on accessory atrioventricular connections," *Circulation* 81(1):86-90.

Mushahwar, V. and Korch, K., (2000) "Muscle recruitment through electrical stimulation of the lumbo-sacral spinal cord," *IEEE Transactions on Rehabilitation Engineering* 8(1):9-22.

Randall, W. ed., (1977) "Neural Regulation of the Heart", Oxford University Press, particularly pp. 100-106.

Rattay, F., (1989)"Analysis of models for extracellular fiber stimulation," *IEEE Transactions on Biomedical Engineering* 36(2):676-681.

Rijkhoff, N. et al., (1994)"Acute animal studies on the use of anodal block to reduce urethral resistance in sacral root stimulation," *IEEE Transactions on Rehabilitation Engineering*, 2(2):92-99.

Stramba-Badiale, M. (1991)et al., "Sympathetic-Parasympathetic Interaction and Accentuated Antagonism in Conscious Dogs," *American Journal of Physiology* 260 (2Pt 2):H335-340.

Tarver, W. et al., (1992) "Clinical experience with a helical bipolar stimulating lead," *Pace*, vol. 15, October, Part II 1545-1156.

Vanoli, E. et al., (1991) "Vagal stimulation and prevention of sudden death in conscious dogs with a healed myocardial infarction," *Circulation Research* 68(5): 1471-1481.

Veraart, C. et al., (1993) "Selective control of muscle activation with a multipolar nerve cuff electrode," *IEEE Transactions on Biomedical Engineering*, 40(7):640-653.

Wang, H. et al., (2003) "Nicotinic acetylcholine receptor alpha-7 subunit is an essential regulator of inflammation," *Nature* 421:384-388.

Waninger, M. et al., (2000) "Electrophysiological control of ventricular rate during atrial fibrillation," *PACE* 23:1239-1244

* cited by examiner

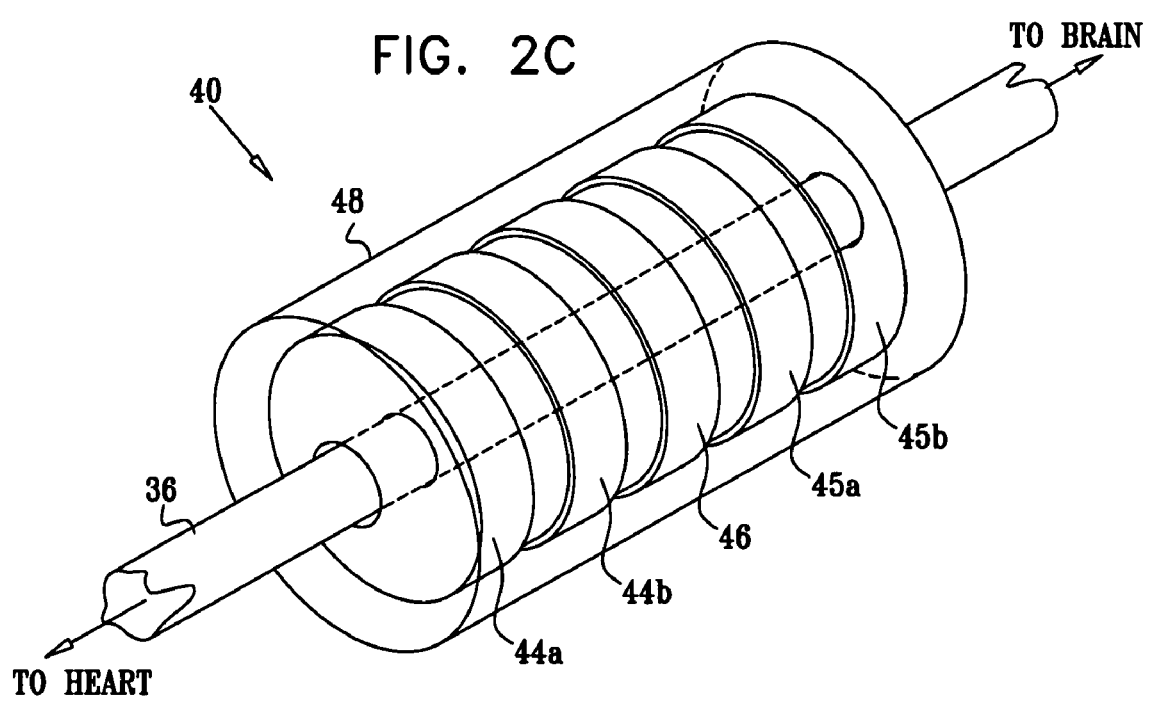

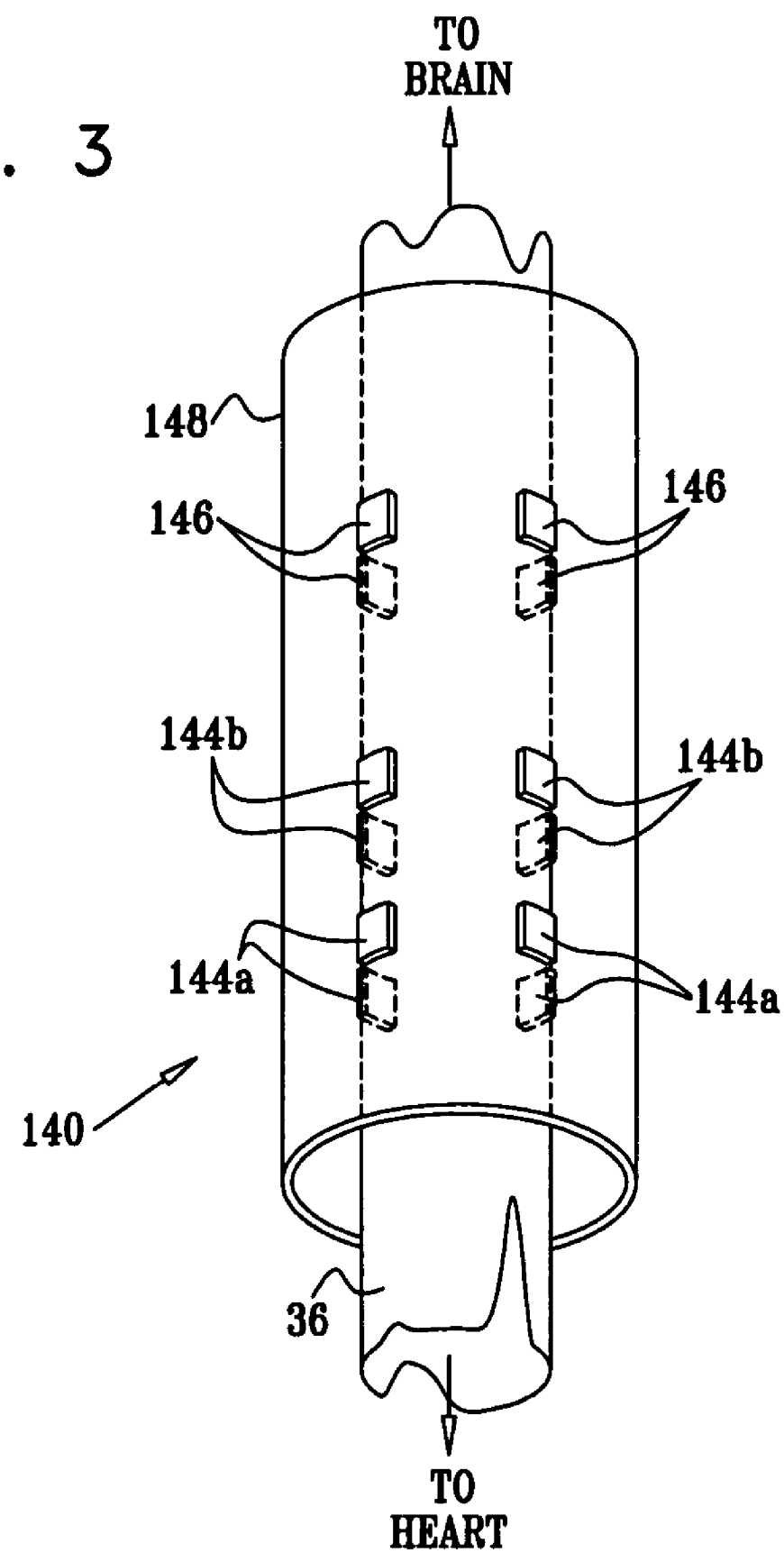

PARASYMPATHETIC STIMULATION FOR TREATING ATRIAL ARRHYTHMIA AND HEART FAILURE

CROSS-REFERENCES TO RELATED APPLICATIONS

The present patent application is a continuation of U.S. Ser. No. 10/719,659, filed Nov. 20, 2003, now U.S. Pat. No. 7,778, 711 entitled, "Selective nerve fiber stimulation for treating heart conditions," which is a continuation-in-part of PCT Patent Application PCT/IL03/00431, filed May 23, 2003, entitled, "Selective nerve fiber stimulation for treating heart conditions," which:

(a) is a continuation-in-part of U.S. patent application Ser. No. 10/205,475, filed Jul. 24, 2002, now U.S. Pat. No. 7,778, 703 entitled, "Selective nerve fiber stimulation for treating heart conditions," which is a continuation-in-part of PCT Patent Application PCT / IL02 / 00068, filed Jan. 23, 2002, entitled, "Treatment of disorders by unidirectional nerve stimulation, " which is a continuation-in-part of U.S. patent application 09/944,913, filed Aug. 31, 2001, entitled, "Treatment of disorders by unidirectional nerve stimulation," which issued as U.S. Pat. No. 6,684,105, and (b) claims the benefit of U.S. Provisional Patent Application 60/383,157 to Ayal et al., filed May 23, 2002, entitled, "Inverse recruitment for autonomic nerve systems."

Each of the above-referenced applications is assigned to the assignee of the present patent application and incorporated herein by reference.

FIELD OF THE INVENTION

The present invention relates generally to treating patients by application of electrical signals to a selected nerve or nerve bundle, and specifically to methods and apparatus for stimulating the vagus nerve for treating heart conditions.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including heart failure and atrial fibrillation. Heart failure is a cardiac condition characterized by a deficiency in the ability of the heart to pump blood throughout the body and/or to prevent blood from backing up in the lungs. Customary treatment of heart failure includes medication and lifestyle changes. It is often desirable to lower the heart rates of patients suffering from faster than normal heart rates. The effectiveness of beta blockers in treating heart disease is attributed in part to their heart-rate-lowering effect.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

U.S. Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," Nervous Control of Vascular Function, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., Neural Regulation of the Heart, Oxford University Press (1977), particularly pages 100-106.

Armour J A et al. eds., Neurocardiology, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Fuster V and Ryden L E et al., "ACC/AHA/ESC Practice Guidelines—Executive Summary," J Am Coll Cardiol 38(4): 1231-65 (2001)

Fuster V and Ryden L E et al., "ACC/AHA/ESC Practice Guidelines—Full Text," J Am Coll Cardiol 38(4):1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharmacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Heart rate variability is considered an important determinant of cardiac function. Heart rate normally fluctuates within a normal range in order to accommodate constantly changing physiological needs. For example, heart rate increases during waking hours, exertion, and inspiration, and decreases during sleeping, relaxation, and expiration. Two representations of heart rate variability are commonly used: (a) the standard deviation of beat-to-beat RR interval differences within a certain time window (i.e., variability in the time domain), and (b) the magnitude of variability as a function of frequency (i.e., variability in the frequency domain).

Short-term (beat-to-beat) variability in heart rate represents fast, high-frequency (HF) changes in heart rate. For example, the changes in heart rate associated with breathing are characterized by a frequency of between about 0.15 and about 0.4 Hz (corresponding to a time constant between about 2.5 and 7 seconds). Low-frequency (LF) changes in heart rate (for example, blood pressure variations) are characterized by a frequency of between about 0.04 and about 0.15 Hz (corresponding to a time constant between about 7 and 25 seconds). Very-low-frequency (VLF) changes in heart rate are characterized by a frequency of between about 0.003 and about 0.04 Hz (0.5 to 5 minutes). Ultra-low-frequency (ULF) changes in heart rate are characterized by a frequency of between about 0.0001 and about 0.003 Hz (5 minutes to 2.75 hours). A commonly used indicator of heart rate variability is the ratio of HF power to LF power.

High heart rate variability (especially in the high frequency range, as described hereinabove) is generally correlated with a good prognosis in conditions such as ischemic heart disease and heart failure. In other conditions, such as atrial fibrillation, increased heart rate variability in an even higher frequency range can cause a reduction in cardiac efficiency by producing beats that arrive too quickly (when the ventricle is not optimally filled) and beats that arrive too late (when the ventricle is fully filled and the pressure is too high).

Kamath et al., in "Effect of vagal nerve electrostimulation on the power spectrum of heart rate variability in man," Pacing Clin Electrophysiol 15:235-43 (1992), describe an increase in the ratio of low frequency to high frequency components of the peak power spectrum of heart rate variability during a period without vagal stimulation, compared to periods with vagal stimulation. Iwao et al., in "Effect of constant and intermittent vagal stimulation on the heart rate and heart rate variability in rabbits," Jpn J Physiol 50:33-9 (2000), describe no change in heart rate variability caused by respiration in all modes of stimulation with respect to baseline data. Each of these articles is incorporated herein by reference.

The following articles, which are incorporated herein by reference, may be of interest:

Kleiger RE et al., "Decreased heart rate variability and its association with increased mortality after myocardial infarction," Am J Cardiol 59: 256-262 (1987)

Akselrod S et al., "Power spectrum analysis of heart rate fluctuation: a quantitative probe of beat-to-beat cardiovascular control," Science 213: 220-222 (1981)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmstrom et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects. The significance of sympathetic and parasympathetic activation are described as being evaluated by determining the effects of autonomic nervous system using vagal and stellar ganglions stimulation, and by using autonomic nervous system neurotransmitters infusion (norepinephrine, acetylcholine).

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. No. 5,334,221 to Bardy and U.S. Pat. No. 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electrostimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

A number of patents and articles describe other methods and devices for stimulating nerves to achieve a desired effect. Often these techniques include a design for an electrode or electrode cuff.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

Levy M N, Blattberg B., "Effect of vagal stimulation on the overflow of norepinephrine into the coronary sinus during sympathetic nerve stimulation in the dog," Circ Res 1976 February; 38(2):81-4

Lavallee et al. "Muscarinic inhibition of endogenous myocardial catecholamine liberation in the dog," Can J Physiol Pharmacol 1978 August; 56(4):642-9

Mann D L, Kent R L, Parsons B, Cooper G, "Adrenergic effects on the biology of the adult mammalian cardiocyte," Circulation 1992 February; 85(2):790-804

Mann D L, "Basic mechanisms of disease progression in the failing heart: role of excessive adrenergic drive," Prog Cardiovasc Dis 1998 July-August; 41(1 suppl 1):1-8

Barzilai A, Daily D, Zilkha-Falb R, Ziv I, Offen D, Melamed E, Sirv A, "The molecular mechanisms of dopamine toxicity," Adv Neurol 2003; 91:73-82

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, $\sigma$ is the conductance tensor specifying the conductance of the various materials (electrode housing, axon, intracellular fluid, etc.), and j is a scalar function representing the current source density specifying the locations of current injection.

SUMMARY OF THE INVENTION

In embodiments of the present invention, apparatus for treating a heart condition comprises a multipolar electrode device that is applied to a portion of a vagus nerve that innervates the heart of a patient. Typically, the system is configured to treat heart failure and/or heart arrhythmia, such as atrial fibrillation or tachycardia. A control unit typically drives the electrode device to (i) apply signals to induce the propagation of efferent action potentials towards the heart, and (ii) suppress artificially-induced afferent and efferent action potentials, in order to minimize any unintended side effect of the signal application.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, a small anodal current is applied in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked, as described above. By not stimulating large-diameter fibers, such stimulation generally avoids adverse effects sometimes associated with recruitment of such large fibers, such as dyspnea and hoarseness. Stimulation of small-diameter fibers is avoided because these fibers transmit pain sensations and are important for regulation of reflexes such as respiratory reflexes.

In some embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set typically comprises a plurality of anodes in order to minimize the virtual cathode effect in the direction of the brain.

In some embodiments of the present invention, the efferent and afferent anode sets each comprise exactly one electrode, which are directly electrically coupled to each other. The cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, an anodal current is applied in order to inhibit action potentials induced by the cathodic current in the large-diameter fibers (e.g., A-fibers), but not in the small-and medium-diameter fibers (e.g., B- and C-fibers). This combination of cathodic and anodal current generally results in the stimulation of medium-diameter fibers (e.g., B-fibers) only.

Typically, parasympathetic stimulation of the vagus nerve is applied responsive to one or more sensed physiological parameters or other parameters, such as heart rate, electrocardiogram (ECG), blood pressure, indicators of cardiac contractility, cardiac output, norepinephrine concentration, baroreflex sensitivity, or motion of the patient. Typically, stimulation is applied in a closed-loop system in order to achieve and maintain a desired heart rate responsive to one or more such sensed parameters.

In some embodiments of the present invention, vagal stimulation is applied in a burst (i.e., a series of pulses). The application of the burst in each cardiac cycle typically commences after a variable delay after a detected R-wave, P-wave, or other feature of an ECG. The delay is typically calculated in real time using a function, the inputs of which include one or more pre-programmed but updateable constants and one or more sensed parameters, such as the R-R interval between cardiac cycles and/or the P-R interval. Alternatively or additionally, a lookup table of delays is used to determine in real time the appropriate delay for each application of pulses, based on the one or more sensed parameters.

In some embodiments of the present invention, the control unit is configured to drive the electrode device to stimulate the vagus nerve so as to reduce the heart rate of the subject towards a target heart rate. Parameters of stimulation are varied in real time in order to vary the heart-rate-lowering effects of the stimulation. In embodiments of the present invention in which the stimulation is applied in a series of pulses that are synchronized with the cardiac cycle of the subject, such as described hereinabove, parameters of such pulse series typically include, but are not limited to: (a) timing of the stimulation within the cardiac cycle, (b) pulse duration (width), (c) pulse repetition interval, (d) pulse period, (e) number of pulses per burst, also referred to herein as "pulses per trigger" (PPT), (f) amplitude, (g) duty cycle, (h) choice of vagus nerve, and (i) "on"/"off" ratio and timing (i.e., during intermittent operation).

In some embodiments of the present invention, the control unit is configured to drive the electrode device to stimulate the vagus nerve so as to modify heart rate variability of the subject. For some applications, the control unit is configured to apply stimulation with parameters that tend to or that are selected to reduce heart rate variability, while for other applications parameters are used that tend to or that are selected to increase variability. For some applications, the parameters of the stimulation are selected to both reduce the heart rate of the subject and heart rate variability of the subject. For other applications, the parameters are selected to reduce heart rate variability while substantially not reducing the heart rate of the subject. For some applications, the control unit is configured to drive the electrode device to stimulate the vagus nerve so as to modify heart rate variability in order to treat a condition of the subject.

Advantageously, the techniques described herein generally enable relatively fine control of the level of stimulation of the vagus nerve, by imitating the natural physiological smaller-to-larger diameter recruitment order of nerve fibers. This recruitment order allows improved and more natural control over the heart rate. Such fine control is particularly advantageous when applied in a closed-loop system, wherein such control results in smaller changes in heart rate and lower latencies in the control loop, which generally contribute to greater loop stability and reduced loop stabilization time.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads, for treatment of heart conditions or other conditions, is also included within the scope of the present invention.

"Heart failure," as used in the specification and the claims, is to be understood to include all forms of heart failure, including ischemic heart failure, non-ischemic heart failure, and diastolic heart failure.

There is therefore provided, in accordance with an embodiment of the present invention, apparatus for treating a heart condition of a subject, including:

an electrode device, adapted to be coupled to a vagus nerve of the subject; and a control unit, adapted to:

drive the electrode device to apply to the vagus nerve a stimulating current, which is capable of inducing action potentials in a therapeutic direction in a first set and a second set of nerve fibers of the vagus nerve, and drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

Typically, the therapeutic direction is an efferent therapeutic direction towards a heart of the subject. Alternatively or additionally, the therapeutic direction is an afferent therapeutic direction towards a brain of the subject.

In an embodiment, the control unit increases a number of action potentials traveling in the therapeutic direction by decreasing an amplitude of the applied inhibiting current, and/or decreases a number of action potentials traveling in the therapeutic direction by increasing an amplitude of the applied inhibiting current.

In an embodiment, the heart condition includes heart failure and/or cardiac arrhythmia, and the apparatus is adapted to treat the heart condition.

Optionally, the apparatus includes an override, adapted to be used by the subject so as to influence the application by the electrode device of the stimulating and inhibiting currents.

In an embodiment, the apparatus includes a pacemaker, and the control unit is adapted to drive the pacemaker to apply pacing pulses to a heart of the subject. Alternatively, the apparatus includes an implantable cardioverter defibrillator (ICD), and the control unit is adapted to drive the ICD to apply energy to a heart of the subject.

Typically, the control unit is adapted to drive the electrode device to apply the stimulating current and/or the inhibiting current in a series of pulses.

In an embodiment, the control unit receives an electrical signal from the electrode device, and drives the electrode device to regulate the stimulating and/or inhibiting current responsive to the electrical signal.

Typically, the electrode device includes a cathode, adapted to apply the stimulating current, and a primary set of anodes, which applies the inhibiting current. For some applications, the primary set of anodes includes a primary anode and a secondary anode, disposed so that the primary anode is located between the secondary anode and the cathode, and the secondary anode applies a current with an amplitude less than about one half an amplitude of a current applied by the primary anode.

Typically, the control unit is adapted to drive the electrode device to apply the stimulating current so as to regulate a heart rate of the subject. For some applications, the control unit is adapted to drive the electrode device to regulate an amplitude of the stimulating current so as to regulate the heart rate of the subject.

Alternatively or additionally, the control unit drives the electrode device to apply the inhibiting current so as to regulate a heart rate of the subject. In this case, the control unit typically drives the electrode device to regulate an amplitude of the inhibiting current so as to regulate the heart rate of the subject.

Typically, the control unit is adapted to drive the electrode device to apply the stimulating and inhibiting currents in a series of pulses. For some applications, the control unit:
  drives the electrode device to apply the stimulating and inhibiting currents in a series of about one to 20 pulses,
  configures the pulses to have a duration of between about one and three milliseconds, and/or
  drives the electrode device to apply the stimulating and inhibiting currents in the series of pulses over a period of between about one and about 200 milliseconds.

Typically, the control unit drives the electrode device to apply the stimulating and inhibiting currents in the series of pulses so as to regulate a heart rate of the subject. For some applications, the control unit regulates the number of pulses in the series of pulses so as to regulate the heart rate of the subject. Optionally, the control unit regulates a duration of each pulse so as to regulate the heart rate of the subject. Optionally, the control unit varies a length of a period of application of the series of pulses so as to regulate the heart rate of the subject.

In an embodiment, the control unit drives the electrode device to apply to the vagus nerve a second inhibiting current, which is capable of inhibiting device-induced action potentials traveling in a non-therapeutic direction opposite the therapeutic direction in the first and second sets of nerve fibers.

Typically, the control unit drives the electrode device to apply the second inhibiting current to the vagus nerve at a primary and a secondary location, the primary location located between the secondary location and an application location of the stimulating current, and to apply at the secondary location a current with an amplitude less than about one half an amplitude of a current applied at the primary location.

In an embodiment, the apparatus includes a sensor unit, and the control unit is adapted to receive at least one sensed parameter from the sensor unit, and to drive the electrode device to apply the stimulating and inhibiting currents responsive to the at least one sensed parameter.

Typically, the control unit is programmed with a predetermined target heart rate, or is adapted to determine a target heart rate of the subject responsive to the at least one sensed parameter, and the control unit is adapted to drive the electrode device to apply the stimulating and inhibiting currents so as to adjust a heart rate of the subject towards the target heart rate.

The sensor unit may include one or more of the following sensors, in which case the control unit receives the at least one sensed parameter from the following one or more sensors:
  a blood pressure sensor,
  a left ventricular pressure (LVP) sensor,
  an accelerometer (in which case, the at least one sensed parameter includes motion of the subject),
  a detector of norepinephrine concentration in the subject,
  an ECG sensor,
  a respiration sensor, and/or
  an impedance cardiography sensor.

Alternatively or additionally, the at least one sensed parameter includes an indicator of decreased cardiac contractility, an indicator of cardiac output, and/or an indicator of a time derivative of a LVP, and the control unit receives the indicator.

In an embodiment, the sensor unit includes an electrocardiogram (ECG) monitor, the at least one sensed parameter includes an ECG value, and the control unit receives the at least one sensed parameter from the ECG monitor.

Typically, the at least one sensed parameter includes an ECG reading indicative of a presence of arrhythmia, and the control unit is adapted to receive the at least one sensed parameter from the ECG monitor. Optionally, the at least one sensed parameter includes an indication of a heart rate of the subject, and the control unit is adapted to receive the indication of the heart rate. Further optionally, the at least one sensed parameter includes indications of a plurality of heart rates of the subject at a respective plurality of points in time, and the control unit is adapted to receive the at least one sensed parameter and to determine a measure of variability of heart rate responsive thereto.

In an embodiment, the sensor unit is adapted to sense an initiation physiological parameter and a termination physiological parameter of the subject, and the control unit is adapted to drive the electrode device to apply the stimulating and inhibiting currents to the vagus nerve after a delay, to initiate the delay responsive to the sensing of the initiation physiological parameter, and to set a length of the delay responsive to the termination physiological parameter.

Typically, the control unit is adapted to determine a target heart rate of the subject responsive to the at least one sensed parameter, and the control unit is adapted to set the delay so as to adjust the heart rate towards the target heart rate.

Optionally, the termination physiological parameter includes an atrioventricular (AV) delay of the subject, and the control unit is adapted to set the length of the delay responsive to the AV delay.

Typically, the sensor unit includes an electrocardiogram (ECG) monitor, and the initiation physiological parameter includes a P-wave or R-wave of a cardiac cycle of the subject, and wherein the control unit is adapted to initiate the delay responsive to the sensing of the P-wave or R-wave, as the case may be. Typically, the termination physiological parameter includes a difference in time between two features of an ECG signal recorded by the ECG monitor, such as an R-R interval between a sensing of an R-wave of a first cardiac cycle of the subject and a sensing of an R-wave of a next cardiac cycle of the subject, or a P-R interval between a sensing of a P-wave of a cardiac cycle of the subject and a sensing of an R-wave of the cardiac cycle, and the control unit sets the length of the delay and/or the magnitude of the stimulation responsive to the termination physiological parameter.

There is further provided, in accordance with an embodiment of the present invention, apparatus for treating a heart condition of a subject, including:

a cathode, adapted to apply to a vagus nerve of the subject a stimulating current which is capable of inducing action potentials in the vagus nerve; and a primary and a secondary anode, adapted to be disposed so that the primary anode is located between the secondary anode and the cathode, and adapted to apply to the vagus nerve respective primary and secondary inhibiting currents which are capable of inhibiting action potentials in the vagus nerve.

Typically, the primary and secondary anodes are adapted to be placed between about 0.5 and about 2.0 millimeters apart from one another. The secondary anode is typically adapted to apply the secondary inhibiting current with an amplitude equal to between about 2 and about 5 milliamps. The secondary anode is typically adapted to apply the secondary inhibiting current with an amplitude less than about one half an amplitude of the primary inhibiting current applied by the primary anode.

In an embodiment, the primary anode, the secondary anode, and/or the cathode includes a ring electrode adapted to apply a generally uniform current around a circumference of the vagus nerve. Alternatively or additionally, the primary anode, the secondary anode, and/or the cathode includes a plurality of discrete primary anodes, adapted to be disposed at respective positions around an axis of the vagus nerve.

Optionally, the apparatus includes a tertiary anode, adapted to be disposed such that the secondary anode is between the tertiary anode and the primary anode.

Typically, the electrode device includes an efferent edge, and the cathode is adapted to be disposed closer than the anodes to the efferent edge of the electrode device.

Typically, the cathode and/or the anodes are adapted to apply the stimulating current so as to regulate a heart rate of the subject.

Optionally, the cathode includes a plurality of discrete cathodes, adapted to be disposed at respective positions around an axis of the vagus nerve, so as to selectively stimulate nerve fibers of the vagus nerve responsive to the positions of the nerve fibers in the vagus nerve.

Optionally, the apparatus includes a set of one or more blocking anodes, adapted to be disposed such that the cathode is between the set of blocking anodes and the primary anode, and adapted to apply to the vagus nerve a current which is capable of inhibiting action potentials propagating in the vagus nerve in a direction from the cathode towards the set of blocking anodes.

Typically, the set of blocking anodes includes a first anode and a second anode, adapted to be disposed such that the first anode is located between the second anode and the cathode, and wherein the second anode is adapted to apply a current with an amplitude less than about one half an amplitude of a current applied by the first anode.

Typically, the electrode device includes an afferent edge, wherein the cathode is adapted to be disposed closer than the anodes to the afferent edge of the electrode device.

Typically, the apparatus includes a cuff, and an electrically-insulating element coupled to an inner portion of the cuff, and the primary anode and the cathode are adapted to be mounted in the cuff and separated from one another by the insulating element. Typically, the primary and secondary anodes and the cathode are recessed in the cuff so as not to be in direct contact with the vagus nerve.

Typically, the apparatus includes a control unit, adapted to drive the cathode and the anodes to apply the respective currents to the vagus nerve, so as to treat the subject.

Typically, the cathode is adapted to apply the stimulating current and the anodes are adapted to apply the inhibiting current so as to regulate a heart rate of the subject. Optionally, the cathode is adapted to vary an amplitude of the applied stimulating current and the anodes are adapted to vary an amplitude of the applied inhibiting current so as to regulate a heart rate of the subject.

Typically, the control unit is adapted to:

drive the electrode device to apply to the vagus nerve a stimulating current, which is capable of inducing action potentials in a therapeutic direction in a first set and a second set of nerve fibers of the vagus nerve, and drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

Optionally, the termination physiological parameter includes a blood pressure of the subject, and wherein the control unit is adapted to set the length of the delay responsive to the blood pressure.

Typically, the sensor unit is adapted to sense a rate-setting parameter of the subject, wherein the rate-setting parameter includes a blood pressure of the subject, and wherein the control unit is adapted to receive the rate-setting parameter from the sensor unit and to drive the electrode device to apply the current responsive to the rate-setting parameter.

Optionally, the rate-setting parameter includes the initiation physiological parameter and/or the termination physiological parameter, and the control unit is adapted to drive the electrode device to apply the current responsive to the initiation physiological parameter so as to regulate the heart rate of the subject.

Typically, the control unit is adapted to set the length of the delay so as to adjust the heart rate towards the target heart rate. Optionally, the control unit is adapted to access a lookup table of delays, and to set the length of the delay using the lookup table and responsive to the initiation and termination physiological parameters.

Typically, the initiation physiological parameter includes a P-wave, R-wave, Q-wave, S-wave, or T-wave of a cardiac cycle of the subject, and wherein the control unit is adapted to initiate the delay responsive to the sensing of the cardiac wave.

Typically, the termination physiological parameter includes a difference in time between two features of an ECG signal recorded by the ECG monitor, and the control unit is adapted to set the length of the delay responsive to the difference in time between the two features. The termination physiological parameter may include an R-R interval between a sensing of an R-wave of a first cardiac cycle of the subject and a sensing of an R-wave of a next cardiac cycle of the subject, and wherein the control unit is adapted to set the length of the delay responsive to the R-R interval. Alternatively or additionally, the termination physiological parameter includes an average of R-R intervals sensed for a number of cardiac cycles, and wherein the control unit is adapted to set the length of the delay responsive to the average of the R-R intervals.

Alternatively, the termination physiological parameter includes a P-R interval between a sensing of a P-wave of a cardiac cycle of the subject and a sensing of an R-wave of the cardiac cycle, and wherein the control unit is adapted to set the length of the delay responsive to the P-R interval. Alternatively or additionally, the termination physiological parameter includes an average of P-R intervals sensed for a number of cardiac cycles, and wherein the control unit is adapted to set the length of the delay responsive to the average of the P-R intervals.

There is also provided, in accordance with an embodiment of the present invention, apparatus for treating a condition of a subject, including:

an electrode device, adapted to be coupled to an autonomic nerve of the subject; and a control unit, adapted to:

drive the electrode device to apply to the nerve a stimulating current, which is capable of inducing action potentials in a therapeutic direction in a first set and a second set of nerve fibers of the nerve, and drive the electrode device to apply to the nerve an inhibiting current, which is capable of inhibiting the induced action potentials traveling in the therapeutic direction in the second set of nerve fibers, the nerve fibers in the second set having generally larger diameters than the nerve fibers in the first set.

Typically, the autonomic nerve includes the vagus nerve, and the control unit is adapted to drive the electrode device to apply the stimulating and inhibiting currents to the nerve.

Typically, the control unit is adapted to drive the electrode device to apply the stimulating and inhibiting currents to the nerve so as to affect behavior of one of the following, so as to treat the condition:

a lung of the subject, a heart of the subject, an immune system of the subject, and/or an adrenal gland of the subject.

There is additionally provided, in accordance with an embodiment of the present invention, apparatus for treating a condition of a subject, including:

a cathode, adapted to apply to an autonomic nerve of the subject a stimulating current which is capable of inducing action potentials in the nerve; and a primary and a secondary anode, adapted to be disposed so that the primary anode is located between the secondary anode and the cathode, and adapted to apply to the nerve respective primary and secondary inhibiting currents which are capable of inhibiting action potentials in the nerve.

There is yet additionally provided, in accordance with an embodiment of the present invention, a method for treating a heart condition of a subject, including:

applying, to a vagus nerve of the subject, a stimulating current which is capable of inducing action potentials in a therapeutic direction in a first set and a second set of nerve fibers of the vagus nerve; and applying to the vagus nerve an inhibiting current which is capable of inhibiting the induced action potentials traveling in the therapeutic direction in the second set of nerve fibers, the nerve fibers in the second set having generally larger diameters than the nerve fibers in the first set.

There is still additionally provided, in accordance with an embodiment of the present invention, a method for treating a heart condition of a subject, including:

applying, to a vagus nerve of the subject, at a stimulation location, a stimulating current which is capable of inducing action potentials in the vagus nerve, so as to treat the subject; and applying to the vagus nerve at a primary and a secondary location, the primary location located between the secondary location and the stimulation location, an inhibiting current which is capable of inhibiting action potentials in the vagus nerve.

There is still further provided, in accordance with an embodiment of the present invention, a method for treating a condition of a subject, including:

applying, to an autonomic nerve of the subject, a stimulating current which is capable of inducing action potentials in a therapeutic direction in a first set and a second set of nerve fibers of the nerve; and applying to the nerve an inhibiting current which is capable of inhibiting the induced action potentials traveling in the therapeutic direction in the second set of nerve fibers, the nerve fibers in the second set having generally larger diameters than the nerve fibers in the first set.

There is also provided, in accordance with an embodiment of the present invention, a method for treating a condition of a subject, including:

applying, to an autonomic nerve of the subject, at a stimulation location, a stimulating current which is capable of inducing action potentials in the nerve, so as to treat the subject; and applying to the nerve at a primary and a secondary location, the primary location located between the secondary location and the stimulation location, an inhibiting current which is capable of inhibiting action potentials in the nerve.

There is further provided, in accordance with an embodiment of the present invention, apparatus for treating a subject, including:

an electrode device, adapted to be coupled to a vagus nerve of the subject;

a heart rate sensor, configured to detect a heart rate of the subject, and to generate a heart rate signal responsive thereto; and a control unit, adapted to:

receive the heart rate signal, and responsive to determining that the heart rate is greater than a threshold value, which threshold value is greater than a normal heart rate, drive the electrode device to apply a current to the vagus nerve, and configure the current so as to reduce the heart rate of the subject.

For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

Alternatively or additionally, the current includes a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

For some applications, the vagus nerve includes small-, medium-, and large-diameter fibers, and the electrode device includes:

a cathode, adapted to be disposed at a cathodic site of the vagus nerve, and to apply a cathodic current to the vagus nerve which is capable of inducing action potentials in the vagus nerve; and an anode, adapted to be disposed at an anodal site of the vagus nerve, and to apply to the vagus nerve an anodal current which is capable of inhibiting action potentials in the vagus nerve, and the control unit is adapted to:

drive the cathode to apply to the vagus nerve the cathodic current having a cathodic amplitude sufficient to induce action potentials in the medium- and large-diameter fibers, but generally insufficient to induce action potentials in the small-diameter fibers, and drive the anode to apply to the vagus nerve the anodal current having an anodal amplitude sufficient to inhibit action potentials in the large-diameter fibers, but generally insufficient to inhibit action potentials in the medium-diameter fibers.

In an embodiment, the control unit is adapted to utilize a value of at least 100 beats per minute as the threshold value.

In an embodiment, the control unit is adapted to withhold driving the electrode device upon determining that the heart rate is less than a value associated with bradycardia.

In an embodiment, the control unit is adapted to configure the current so as to reduce the heart rate towards a target heart rate.

For some applications, the normal heart rate includes a normal heart rate of the subject. Alternatively, the normal heart rate includes a normal heart rate of a typical human.

In an embodiment, the control unit is adapted to drive the electrode device to apply the current with an amplitude of between about 2 and about 10 milliamps.

In an embodiment, the control unit is adapted to drive the electrode device to apply the current in intermittent ones of a plurality of cardiac cycles of the subject.

In an embodiment, the apparatus includes an electrode selected from the list consisting of: an electrode for pacing the heart, and an electrode for defibrillating the heart, and the control unit is adapted to withhold driving the electrode device to apply the current to the vagus nerve if the control unit is driving the electrode selected from the list.

In an embodiment, the control unit is adapted to drive the electrode device to apply the current in respective pulse bursts in each of a plurality of cardiac cycles of the subject. The control unit may be adapted to configure each pulse of each of the bursts to have a pulse duration of between about 0.2 and about 4 milliseconds. The control unit may be adapted to configure each of the bursts to have a pulse repetition interval of greater than about 3 milliseconds. Alternatively or additionally, the control unit is adapted to configure at least one of the bursts to have between about 0 and about 8 pulses.

In an embodiment, the apparatus includes an electrocardiogram (ECG) monitor, adapted to generate an ECG signal, and the control unit is adapted to receive the ECG signal, and to initiate the applying of each burst after a delay following detection of a feature of the ECG.

There is still further provided, in accordance with an embodiment of the present invention, apparatus for applying current to a vagus nerve, including:

a cathode, adapted to be disposed at a cathodic site of the vagus nerve and to apply a cathodic current to the vagus nerve so as to stimulate the vagus nerve;

a first anode, adapted to be disposed at a first anodal site of the vagus nerve; and a second anode, directly electrically connected to the first anode, and adapted to be disposed at a second anodal site of the vagus nerve, such that the cathodic site is between the first anodal site and the second anodal site.

In an embodiment, the cathode and anodes are disposed such that the cathodic site is disposed closer to the first anodal site than to the second anodal site.

In an embodiment, the nerve includes small-, medium-, and large-diameter fibers, and the apparatus includes a control unit, adapted to:

drive the cathode to apply to the vagus nerve the cathodic current having a cathodic amplitude sufficient to induce action potentials in the medium- and large-diameter fibers, but generally insufficient to induce action potentials in the small-diameter fibers, and drive the first and second anodes to apply to the vagus nerve an anodal current having an anodal amplitude sufficient to inhibit action potentials in the large-diameter fibers, but generally insufficient to inhibit action potentials in the medium-diameter fibers.

In an embodiment, the apparatus includes:

a control unit; and an electrode selected from the list consisting of: an electrode for pacing the heart, and an electrode for defibrillating the heart, and the control unit is adapted to drive current through the cathode and the first and second anodes, and the control unit is adapted to withhold driving current through the cathode and the first and second anodes if the control unit is driving current through the electrode selected from the list.

In an embodiment, the apparatus includes a control unit, adapted to:

drive the cathode to apply the cathodic current, configure the cathodic current to induce action potentials in a first set and a second set of nerve fibers of the vagus nerve, the nerve fibers in the second set having generally larger diameters than the nerve fibers in the first set, drive an anodal current to the first and second anodes, whereby the first and second anodes apply current to the vagus nerve at levels corresponding to respective first and second anodal currents, and configure the anodal current driven to the first and second anodes to inhibit the induced action potentials traveling in the second set of nerve fibers.

In an embodiment, the first and second anodes are configured such that a level of impedance between the first anode and the cathode is lower than a level of impedance between the second anode and the cathode, the control unit is adapted to configure the anodal current driven to the first and second anodes such that the first anodal current inhibits the induced action potentials traveling in the first set of nerve fibers, and the control unit is adapted to configure the anodal current driven to the first and second anodes to be such that the second anodal current is generally insufficient to inhibit the induced action potentials traveling in the first set of nerve fibers.

There is additionally provided, in accordance with an embodiment of the present invention, apparatus for treating a subject, including:

an electrode device, adapted to be coupled to a vagus nerve of the subject;

a sensor, configured to detect a heart rate of the subject, and to generate a heart rate signal responsive thereto; and a control unit including an integral feedback controller that has inputs including the detected heart rate and a target heart rate, the control unit adapted to:

drive the electrode device to apply a current to the vagus nerve, and configure the current responsive to an output of the integral feedback controller, so as to reduce the heart rate of the subject toward a target heart rate.

In an embodiment, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the current includes a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the vagus nerve includes small-, medium-, and large-diameter fibers, and the electrode device includes:

a cathode, adapted to be disposed at a cathodic site of the vagus nerve, and to apply a cathodic current to the vagus nerve which is capable of inducing action potentials in the vagus nerve; and an anode, adapted to be disposed at an anodal site of the vagus nerve, and to apply to the vagus nerve an anodal current which is capable of inhibiting action potentials in the vagus nerve, and the control unit is adapted to:

drive the cathode to apply to the vagus nerve the cathodic current having a cathodic amplitude sufficient to induce action potentials in the medium- and large-diameter fibers, but generally insufficient to induce action potentials in the small-diameter fibers, and drive the anode to apply to the vagus nerve the anodal current having an anodal amplitude sufficient to inhibit action potentials in the large-diameter fibers, but generally insufficient to inhibit action potentials in the medium-diameter fibers.

In an embodiment, the control unit is adapted to change the parameter by:

determining a target value of the parameter, which target value is substantially appropriate for achieving the target heart rate, determining an intermediate value for the parameter, the intermediate value between a current value of the parameter and the target value of the parameter, and setting the parameter at the intermediate value.

In an embodiment, the control unit is adapted to withhold driving the electrode device upon determining that the heart rate is less than a value associated with bradycardia.

In an embodiment, the control unit is adapted to drive the electrode device to apply the current with an amplitude of between about 2 and about 10 milliamps.

In an embodiment, the control unit is adapted to drive the electrode device to apply the current in intermittent ones of a plurality of cardiac cycles of the subject.

In an embodiment, the apparatus includes an electrode selected from the list consisting of: an electrode for pacing the heart, and an electrode for defibrillating the heart, and the control unit is adapted to withhold driving the electrode device to apply the current to the vagus nerve when the control unit drives the electrode selected from the list.

In an embodiment, the integral feedback controller is adapted to calculate a difference between the target heart rate and the detected heart rate, and the control unit is adapted to set a level of a stimulation parameter of the current responsive to a summation over time of the difference.

In an embodiment, the control unit is adapted to set a level of a stimulation parameter of the current by selecting the level from fewer than 16 discrete values. For some applications, the control unit is adapted to set the level of the stimulation parameter of the current by selecting the level from fewer than 10 discrete values. For some applications, the level of the stimulation parameter of the current includes a number of pulses to apply during a cardiac cycle, and the control unit is adapted to set the number to be a number between 0 and 16.

For some applications, when a value of the level of the stimulation parameter suitable to achieve the target heart rate is between two of the discrete values, the control unit is adapted to vary the level, in turns, between the two of the discrete values. For some applications, when the suitable value of the level is between the two discrete values, the control unit is adapted to vary the level from a first one of the two discrete values, to a second one of the two discrete values, and back to the first one of the two discrete values, in a time period lasting fewer than 20 heartbeats. For some applications, when the suitable value of the level is between the two discrete values, the control unit is adapted to vary the level from a first one of the two discrete values, to a second one of the two discrete values, and back to the first one of the two discrete values, in a time period lasting fewer than 10 heartbeats.

In an embodiment, the control unit is adapted to drive the electrode device to apply the current in respective pulse bursts in each of a plurality of cardiac cycles of the subject. The at least one parameter may include a number of pulses per burst, and the control unit is adapted to change the at least one parameter by changing the number of pulses per burst no more than once in any given approximately 15-second period during operation of the apparatus. Alternatively or additionally, the at least one parameter includes a number of pulses per burst, and the control unit is adapted to change the at least one parameter by changing, during any given approximately 15-second period during operation of the apparatus, the number of pulses per burst by no more than one pulse.

In an embodiment, the control unit is adapted to configure each pulse of each of the bursts to have a pulse duration of between about 0.2 and about 4 milliseconds. In an embodiment, the control unit is adapted to configure each of the bursts to have a pulse repetition interval of greater than about 3 milliseconds.

In an embodiment, the control unit is adapted to configure at least one of the bursts to have between about 0 and about 8 pulses.

In an embodiment, the apparatus includes an electrocardiogram (ECG) monitor, adapted to measure an ECG signal, the control unit is adapted to receive the ECG signal, and to initiate the applying of each burst after a delay following detection of a feature of the ECG.

In an embodiment, the control unit is adapted to set a control parameter of a feedback algorithm governing the current application to be a number of pulses per burst.

In an embodiment, the at least one parameter includes a number of pulses per burst, and the control unit is adapted to change the at least one parameter by changing, over the period, the number of pulses per burst by less than about three pulses. For some applications, the control unit is adapted to change the at least one parameter by changing, over the period, the number of pulses per burst by exactly one pulse. Alternatively or additionally, the control unit is adapted to change the at least one parameter by changing, during each of two consecutive periods, the number of pulses per burst by less than about three pulses, each of the two consecutive periods having a duration of at least about 15 seconds. The control unit may be adapted to change the at least one parameter by changing, during each of the two consecutive periods, the number of pulses per burst by exactly one pulse.

In an embodiment, the control unit is adapted to change the at least one parameter at a rate of change, the rate of change determined at least in part responsive to a heart rate variable selected from: an R-R interval of the subject and a time derivative of the heart rate of the subject. For some applications, the control unit is adapted to increase the rate of change as the heart rate approaches a threshold limit greater than a normal heart rate of the subject. For other applications, the control unit is adapted to increase the rate of change as the heart rate approaches a threshold limit less than a normal heart rate of the subject. Alternatively or additionally, the control unit is adapted to decrease the rate of change as the heart rate increases, and to increase the rate of change as the heart rate decreases.

In an embodiment, the control unit is adapted to use a time derivative of an R-R interval of the subject as an input to a feedback algorithm governing the current application.

In an embodiment, the control unit is adapted to correct for an absence of an expected heartbeat.

For some applications, the control unit is adapted to sense an R-R interval and: (a) store the sensed R-R interval, if the sensed R-R interval is less than a threshold value, and (b) store the threshold value, if the sensed R-R interval is greater than the threshold value.

In an embodiment, the control unit is adapted to cycle between "on" periods, during which the control unit drives the electrode device to apply the current, and "off" periods, during which the control unit withholds driving the electrode device. For some applications, the control unit is adapted to determine a desired level of stimulation applied by the electrode device, and to configure the cycling between the "on" and "off" periods responsive to the desired level of stimulation. For some applications, the control unit is adapted to set each of the "on" periods to have a duration of less than about 300 seconds. For some applications, the control unit is adapted to set each of the "off" periods to have a duration of between about 0 and about 300 seconds.

In an embodiment, the control unit is adapted to set the parameter at a beginning of one of the "on" periods equal to a value of the parameter at an end of an immediately preceding one of the "on" periods. In an embodiment, the control unit is adapted to configure the current using an algorithm that disregards between about one and about five heart beats at a beginning of each of the "on" periods.

In an embodiment, the control unit is adapted to set the target heart rate during at least one of the "on" periods at least in part responsive to a historic heart rate sensed during a preceding one of the "off" periods. The control unit may be adapted to set the target heart rate during the at least one of the "on" periods at least in part responsive to a historic heart rate sensed during an immediately preceding one of the "off" periods.

There is yet additionally provided, in accordance with an embodiment of the present invention, apparatus for treating a heart condition of a subject, including:

an electrode device, adapted to be coupled to a vagus nerve of the subject; and a control unit, adapted to cycle between "on" periods, during which the control unit drives the electrode device to apply a current to the vagus nerve, and "off" periods, during which the control unit withholds driving the electrode device, so as to treat the heart condition.

In an embodiment, the control unit is adapted to withhold driving the electrode device upon determining that the heart rate is less than a value associated with bradycardia. In an embodiment, the control unit is adapted to drive the electrode device to apply the current with an amplitude of between about 2 and about 10 milliamps. In an embodiment, the control unit is adapted to drive the electrode device to apply the current in intermittent ones of a plurality of cardiac cycles of the subject.

In an embodiment, the apparatus includes an electrode selected from the list consisting of: an electrode for pacing the heart, and an electrode for defibrillating the heart, and the control unit is adapted to withhold driving the electrode device to apply the current to the vagus nerve during an "on" period if the control unit is driving the electrode selected from the list.

In an embodiment, the control unit is adapted to drive the electrode device to apply the current in respective pulse bursts in each of a plurality of cardiac cycles of the subject. For some applications, the control unit is adapted to configure each pulse of each of the bursts to have a pulse duration of between about 0.2 and about 4 milliseconds. For some applications, the control unit is adapted to configure each of the bursts to have a pulse repetition interval of greater than about 3 milliseconds. For some applications, the control unit is adapted to configure at least one of the bursts to have between about 0 and about 8 pulses. In an embodiment, the apparatus includes an electrocardiogram (ECG) monitor, adapted to measure an ECG signal, the control unit is adapted to receive the ECG signal, and to initiate the applying of each burst after a delay following detection of a feature of the ECG.

In an embodiment, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the current includes a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the vagus nerve includes small-, medium-, and large-diameter fibers, and the electrode device includes:

a cathode, adapted to be disposed at a cathodic site of the vagus nerve, and to apply a cathodic current to the vagus nerve which is capable of inducing action potentials in the vagus nerve; and an anode, adapted to be disposed at an anodal site of the vagus nerve, and to apply to the vagus nerve an anodal current which is capable of inhibiting action potentials in the vagus nerve, and the control unit is adapted to:

drive the cathode to apply to the vagus nerve the cathodic current having a cathodic amplitude sufficient to induce action potentials in the medium- and large-diameter fibers, but generally insufficient to induce action potentials in the small-diameter fibers, and drive the anode to apply to the vagus nerve the anodal current having an anodal amplitude sufficient to inhibit action potentials in the large-diameter fibers, but generally insufficient to inhibit action potentials in the medium-diameter fibers.

There is also provided, in accordance with an embodiment of the present invention, apparatus for treating a subject, including:

an electrode device, adapted to be coupled to a vagus nerve of the subject;

a sensor, configured to detect a heart rate of the subject, and to generate a heart rate signal responsive thereto; and a control unit, adapted to:

receive the heart rate signal, drive the electrode device to apply a current to the vagus nerve, and configure the current to increase a variability of the heart rate.

In an embodiment, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the current includes a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the vagus nerve includes small-, medium-, and large-diameter fibers, and the electrode device includes:

a cathode, adapted to be disposed at a cathodic site of the vagus nerve, and to apply a cathodic current to the vagus nerve which is capable of inducing action potentials in the vagus nerve; and an anode, adapted to be disposed at an anodal site of the vagus nerve, and to apply to the vagus nerve an anodal current which is capable of inhibiting action potentials in the vagus nerve, and the control unit is adapted to:

drive the cathode to apply to the vagus nerve the cathodic current having a cathodic amplitude sufficient to induce action potentials in the medium- and large-diameter fibers, but generally insufficient to induce action potentials in the small-diameter fibers, and drive the anode to apply to the vagus nerve the anodal current having an anodal amplitude sufficient to inhibit action potentials in the large-diameter fibers, but generally insufficient to inhibit action potentials in the medium-diameter fibers.

For some applications, the control unit is adapted to configure the current to increase the variability of the heart rate above a target heart rate variability.

For some applications, the sensor includes an electrocardiogram (ECG) monitor.

For some applications, the control unit is adapted to withhold driving the electrode device upon determining that the heart rate is less than a value associated with bradycardia.

In an embodiment, the control unit is adapted to drive the electrode device to apply the current with an amplitude of between about 2 and about 10 milliamps. In an embodiment, the control unit is adapted to drive the electrode device to apply the current in intermittent ones of a plurality of cardiac cycles of the subject.

In an embodiment, the apparatus includes an electrode selected from the list consisting of: an electrode for pacing the heart, and an electrode for defibrillating the heart, and the control unit is adapted to withhold driving the electrode device to apply the current to the vagus nerve if the control unit is driving the electrode selected from the list.

In an embodiment, the control unit is adapted to drive the electrode device to apply the current in respective pulse bursts in each of a plurality of cardiac cycles of the subject. For some applications, the control unit is adapted to configure each pulse of each of the bursts to have a pulse duration of between about 0.2 and about 4 milliseconds. For some applications, the control unit is adapted to configure each of the bursts to have a pulse repetition interval of greater than about 3 milliseconds. For some applications, the control unit is adapted to configure at least one of the bursts to have between about 0 and about 8 pulses. In an embodiment, the apparatus includes an electrocardiogram (ECG) monitor, adapted to measure an ECG signal, the control unit is adapted to receive the ECG signal, and to initiate the applying of each burst after a delay following detection of a feature of the ECG.

In an embodiment, the control unit is adapted to configure the current using a feedback algorithm.

There is further provided, in accordance with an embodiment of the present invention, a method for treating a subject, including:

detecting a heart rate of the subject; and responsive to determining that the heart rate is greater than a threshold value, which threshold value is greater than a normal heart rate, applying a current to a vagus nerve of the subject, and configuring the current so as to reduce the heart rate of the subject.

There is still further provided, in accordance with an embodiment of the present invention, a method for applying current to a vagus nerve, including:

applying to the vagus nerve, through a common conductor, an anodal current at a first anodal site of the vagus nerve and at a second anodal site of the vagus nerve; and applying a cathodic current to the vagus nerve at a cathodic site of the vagus nerve, so as to stimulate the vagus nerve, the cathodic site disposed between the first anodal site and the second anodal site.

There is additionally provided, in accordance with an embodiment of the present invention, a method for treating a subject, including:

detecting a heart rate of the subject;

applying a current to a vagus nerve of the subject; and configuring the current so as to reduce the heart rate toward a target heart rate, responsive to an output of an integral feedback controller whose inputs include the detected heart rate and a target heart rate.

There is yet additionally provided, in accordance with an embodiment of the present invention, a method for treating a heart condition of a subject, including:

cycling between "on" and "off" periods;

during the "on" periods, applying a current to a vagus nerve of the subject; and during the "off" periods, withholding applying the current, so as to treat the heart condition.

There is also provided, in accordance with an embodiment of the present invention, a method for treating a subject, including:

detecting a heart rate of the subject;

applying a current to a vagus nerve of the subject; and configuring the current to increase a variability of the heart rate.

There is further provided, in accordance with an embodiment of the present invention, apparatus for treating a subject suffering from a heart condition, including:

an electrode device, adapted to be coupled to a vagus nerve of the subject; and a control unit, adapted to drive the electrode device to apply a current to the vagus nerve, and to configure the current to suppress an adrenergic system of the subject, so as to treat the subject.

In an embodiment, the heart condition includes heart failure, and the control unit is adapted to configure the current to treat the heart failure.

There is still further provided, in accordance with an embodiment of the present invention, apparatus for treating a subject suffering from a heart condition, including:

an electrode device, adapted to be coupled to a vagus nerve of the subject; and a control unit, adapted to drive the electrode device to apply a current to the vagus nerve, and to configure the current to modulate contractility of at least a portion of a heart of the subject, so as to treat the subject.

In an embodiment, the control unit is adapted to configure the current to reduce atrial and ventricular contractility.

In an embodiment, the heart condition includes hypertrophic cardiopathy, and the control unit is adapted to configure the current so as to treat the hypertrophic cardiopathy.

There is additionally provided, in accordance with an embodiment of the present invention, apparatus for treating a subject suffering from a heart condition, including:

an electrode device, adapted to be coupled to a vagus nerve of the subject; and a control unit, adapted to drive the electrode device to apply a current to the vagus nerve, and to configure the current to increase coronary blood flow, so as to treat the subject.

In an embodiment, the heart condition is selected from the list consisting of: myocardial ischemia, ischemic heart disease, heart failure, and variant angina, and the control unit is adapted to configure the current to increase the coronary blood flow so as to treat the selected heart condition.

There is yet additionally provided, in accordance with an embodiment of the present invention, a treatment method, including:

identifying a subject suffering from a heart condition;

applying a current to a vagus nerve of the subject; and configuring the current to suppress an adrenergic system of the subject, so as to treat the subject.

There is also provided, in accordance with an embodiment of the present invention, a treatment method, including:

identifying a subject suffering from a heart condition;

applying a current to a vagus nerve of the subject; and configuring the current to modulate contractility of at least a portion of a heart of the subject, so as to treat the subject.

There is further provided, in accordance with an embodiment of the present invention, a treatment method, including:

identifying a subject suffering from a heart condition;

applying a current to a vagus nerve of the subject; and configuring the current to increase coronary blood flow, so as to treat the subject.

There is still further provided, in accordance with an embodiment of the present invention, apparatus including:

an electrode device, adapted to be coupled to a vagus nerve of a subject; and a control unit, adapted to drive the electrode device to apply to the vagus nerve a current that reduces heart rate variability of the subject.

In an embodiment, the control unit is adapted to configure the current to substantially not reduce a heart rate of the subject.

In an embodiment, the control unit is adapted to configure the current to reduce the heart rate variability by at least 5% below a baseline thereof during a time period in which a heart rate of the subject is not reduced responsive to the current by more than 10% below a baseline thereof.

In an embodiment, the control unit is adapted to configure the current to effect a reduction of a heart rate of the subject while reducing the heart rate variability of the subject.

For some applications, the control unit is adapted to drive the electrode device during exertion by the subject. Alternatively, the control unit is adapted to withhold driving the electrode device when the subject is not experiencing exertion.

For some applications, the control unit is adapted to configure the current to reduce a heart rate variability of the subject having a characteristic frequency between about 0.15 and about 0.4 Hz. Alternatively or additionally, the control unit is adapted to configure the current to reduce a heart rate variability of the subject having a characteristic frequency between about 0.04 and about 0.15 Hz.

For some applications, the control unit is adapted to drive the electrode device to apply the current with an amplitude of between about 2 and about 10 milliamps.

For some applications, the control unit is adapted to drive the electrode device to apply the current in intermittent ones of a plurality of cardiac cycles of the subject. For some applications, the control unit is adapted to drive the electrode device to apply the current unsynchronized with a cardiac cycle of the subject.

In an embodiment, the control unit is adapted to drive the electrode device responsive to a circadian rhythm of the subject. For some applications, the control unit is adapted to drive the electrode device when the subject is awake. For some applications, the control unit is adapted to withhold driving the electrode device when the subject is sleeping.

For some applications, the control unit is adapted to drive the electrode device to apply the current in a manner that reduces the heart rate variability by at least 10%. For some applications, the control unit is adapted to drive the electrode device to apply the current in a manner that reduces the heart rate variability by at least 50%.

In an embodiment, the control unit is adapted to drive the electrode device to apply the current in a manner that reduces a standard deviation of a heart rate of the subject within a time window, e.g., a time window that is longer than 10 seconds. For some applications, the standard deviation of the heart rate is reduced by at least about 10% or at least about 50% within the time window that is longer than 10 seconds.

In an embodiment, the control unit is adapted to drive the electrode device to apply the current in respective pulse bursts in each of a plurality of cardiac cycles of the subject.

For some applications, the control unit is adapted to configure each pulse of each of the bursts to have a pulse duration of between about 0.1 and about 4 milliseconds. For some applications, the control unit is adapted to configure each pulse of each of the bursts to have a pulse duration of between about 0.5 and about 2 milliseconds. For some applications, the control unit is adapted to configure each of the bursts to have a pulse repetition interval of between about 2 and about 10 milliseconds. For some applications, the control unit is adapted to configure each of the bursts to have a pulse repetition interval of between about 2 and about 6 milliseconds.

In an embodiment, the apparatus includes a cardiac monitor, adapted to generate a cardiac signal, and the control unit is adapted to receive the cardiac signal, and to initiate the applying of each burst after a delay following detection of a feature of the cardiac signal. For some applications, the control unit is adapted to initiate the applying of each burst after a delay of about 30 to about 200 milliseconds following an R-wave of the cardiac signal. For some applications, the control unit is adapted to initiate the applying of each burst after a delay of about 50 to about 150 milliseconds following an R-wave of the cardiac signal.

For some applications, the control unit is adapted to configure at least one of the bursts to have between about 0 and about 20 pulses. For some applications, the control unit is adapted to configure the bursts to have between about 1 and about 8 pulses during steady state operation.

In an embodiment, the apparatus includes a heart sensor, configured to detect heart activity of the subject, and to generate a heart signal responsive thereto, and the control unit is adapted to receive the heart signal, and, responsive to receiving the heart signal, drive the electrode device to apply the current to the vagus nerve.

For some applications, the control unit is adapted to, responsive to receiving the heart signal, drive the electrode device to apply to the vagus nerve the current synchronized with a cardiac cycle of the subject. For some applications, the control unit is adapted to, responsive to receiving the heart signal, drive the electrode device to apply to the vagus nerve the current unsynchronized with a cardiac cycle of the subject.

In an embodiment, the control unit is adapted to configure the current to reduce a heart rate of the subject.

In an embodiment, the apparatus includes a sensor, configured to detect the heart rate of the subject, and to generate a heart rate signal responsive thereto, and the control unit includes an integral feedback controller that has inputs including the detected heart rate and a target heart rate, and the control unit is adapted to configure the current responsive to an output of the integral feedback controller, so as to reduce the heart rate of the subject toward the target heart rate. For some applications, the target heart rate includes a target normal heart rate within a range of normal heart rates of the subject, and the control unit is adapted to configure the current so as to reduce the heart rate of the subject toward the target normal heart rate.

In an embodiment, the control unit is adapted to configure the current to reduce the heart rate variability so as to treat a condition of the subject. For some applications, the condition includes heart failure of the subject, and the control unit is adapted to configure the current to reduce the heart rate variability by at least about 10% so as to treat the heart failure. For some applications, the condition includes an occurrence of arrhythmia of the subject, and the control unit is adapted to configure the current to reduce the heart rate variability by at least about 10% so as to treat the occurrence of arrhythmia. For some applications, the condition includes atrial fibrillation of the subject, and the control unit is adapted to configure the current to reduce the heart rate variability so as to treat the atrial fibrillation.

There is additionally provided, in accordance with an embodiment of the present invention, a method including applying to a vagus nerve of a subject a current that reduces heart rate variability of the subject.

The present invention will be more fully understood from the following detailed description of an embodiments thereof, taken together with the drawings, in which:

BRIEF DESCRIPTION OF THE DRAWINGS

FIG. 2C is a simplified perspective illustration of the electrode device of FIG. 2A, in accordance with an embodiment of the present invention;

FIG. 3 is a simplified perspective illustration of a multipolar point electrode device applied to a vagus nerve, in accordance with an embodiment of the present invention;

DETAILED DESCRIPTION OF EMBODIMENTS

Figure 1:
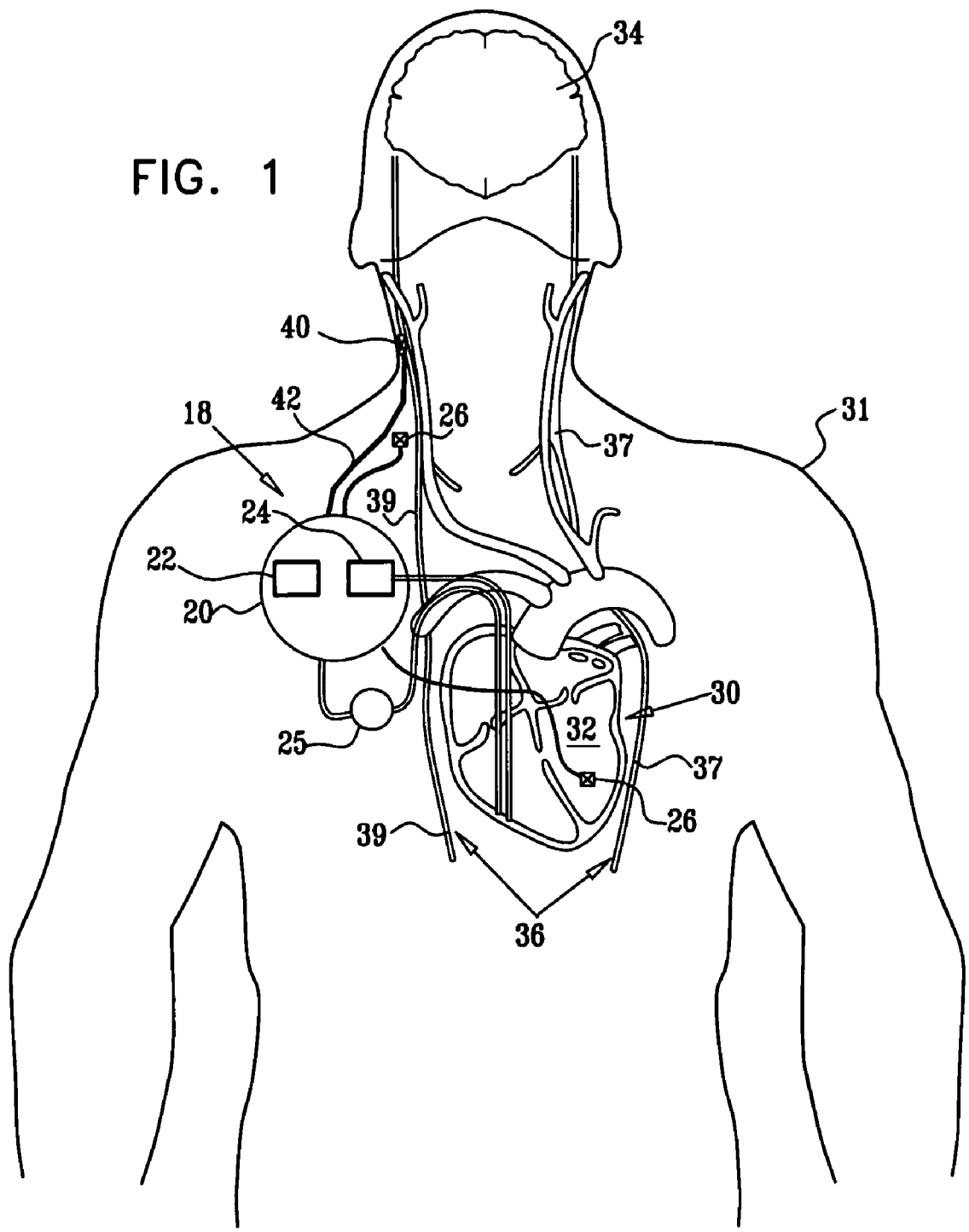
FIG. 1 is a block diagram that schematically illustrates a vagal stimulation system applied to a vagus nerve of a patient, in accordance with an embodiment of the present invention.

FIG. 1 is a block diagram that schematically illustrates a vagal stimulation system 18 comprising a multipolar electrode device 40, in accordance with an embodiment of the present invention. Electrode device 40 is applied to a portion of a vagus nerve 36 (either a left vagus nerve 37 or a right vagus nerve 39), which innervates a heart 30 of a patient 31. Typically, system 18 is utilized for treating a heart condition such as heart failure and/or cardiac arrhythmia. Vagal stimulation system 18 further comprises an implanted or external control unit 20, which typically communicates with electrode device 40 over a set of leads 42. Control unit 20 drives electrode device 40 to (i) apply signals to induce the propagation of efferent nerve impulses towards heart 30, and (ii) suppress artificially-induced afferent nerve impulses towards a brain 34 of the patient, in order to minimize unintended side effects of the signal application. The efferent nerve pulses in vagus nerve 36 are induced by electrode device 40 in order to regulate the heart rate of the patient.

For some applications, control unit 20 is adapted to receive feedback from one or more of the electrodes in electrode device 40, and to regulate the signals applied to the electrode device responsive thereto.

Control unit 20 is typically adapted to receive and analyze one or more sensed physiological parameters or other parameters of the patient, such as heart rate, electrocardiogram (ECG), blood pressure, indicators of decreased cardiac contractility, cardiac output, norepinephrine concentration, or motion of the patient. In order to receive these sensed parameters, control unit 20 may comprise, for example, an ECG monitor 24, connected to a site on the patient's body such as heart 30, for example using one or more subcutaneous sensors or ventricular and/or atrial intracardiac sensors. The control unit may also comprise an accelerometer 22 for detecting motion of the patient. Alternatively, ECG monitor 24 and/or accelerometer 22 comprise separate implanted devices placed external to control unit 20, and, optionally, external to the patient's body. Alternatively or additionally, control unit 20 receives signals from one or more physiological sensors 26, such as blood pressure sensors. Sensors 26 are typically implanted in the patient, for example in a left ventricle 32 of heart 30. In an embodiment, control unit 20 comprises or is coupled to an implanted device 25 for monitoring and correcting the heart rate, such as an implantable cardioverter defibrillator (ICD) or a pacemaker (e.g., a bi-ventricular or standard pacemaker). For example, implanted device 25 may be incorporated into a control loop executed by control unit 20, in order to increase the heart rate when the heart rate for any reason is too low.

Figure 2A:
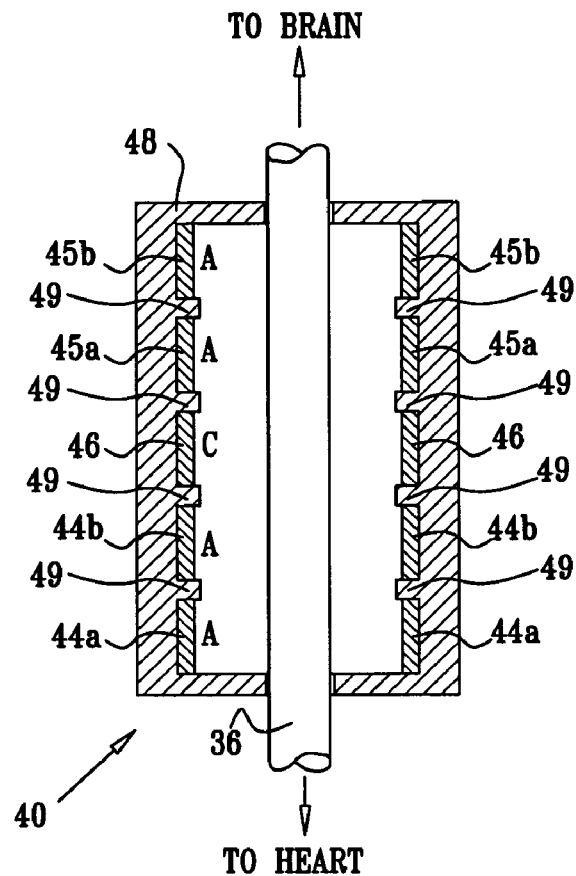
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 40 applied to vagus nerve 36, in accordance with an embodiment of the present invention. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Typically, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 46 is regulated, whereupon more anodal current is driven through the one or more anodes having lower relative impedance. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Figure 2B:
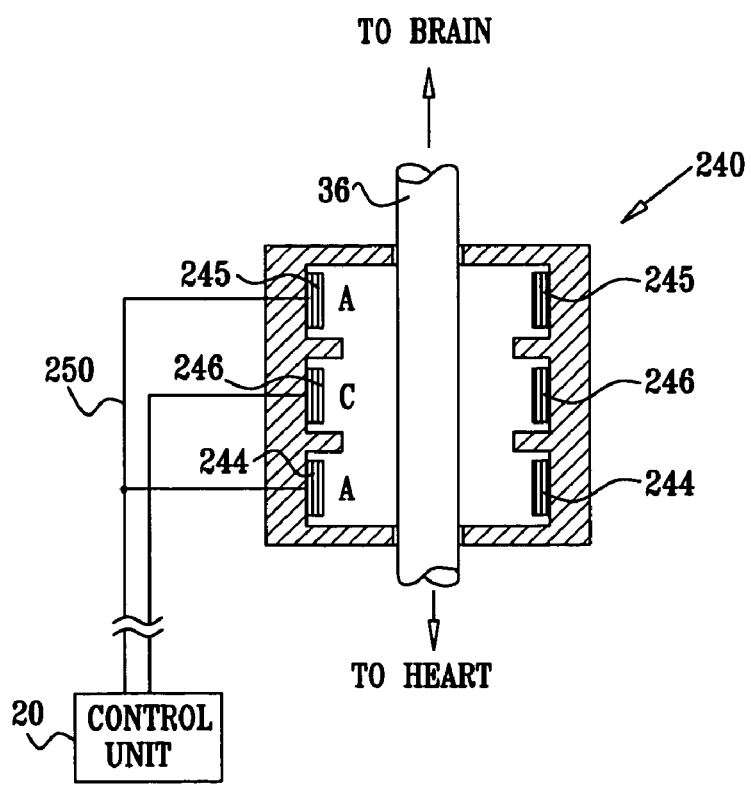
FIG. 2B is a simplified cross-sectional illustration of a generally-cylindrical electrode device applied to a vagus nerve, in accordance with an embodiment of the present invention.

Reference is now made to FIG. 2B, which is a simplified cross-sectional illustration of a generally-cylindrical electrode device 240 applied to vagus nerve 36, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 2A. Cathodes 46 and anode sets 44 and 45 (collectively, "electrodes") are typically mounted in an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 36. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). For some applications, the distance between the ends of protrusions 49 and the center of the vagus nerve is between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 40.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is typically positioned in cuff 48 to apply current at the location on vagus nerve 36 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

As appropriate, techniques described herein are practiced in conjunction with methods and apparatus described in U.S. patent application Ser. No. 10/205,474 to Gross et al., filed Jul. 24, 2002, entitled, "Electrode assembly for nerve control," which published as US Patent Publication 2003/0050677, is assigned to the assignee of the present patent application, and is incorporated herein by reference. Alternatively or additionally, techniques described herein are practiced in conjunction with methods and apparatus described in U.S. patent application Ser. No. 10/205,475 to Gross et al., filed Jul. 24, 2002, entitled, "Selective nerve fiber stimulation for treating heart conditions," which published as US Patent Publication 2003/0045909, is assigned to the assignee of the present patent application, and is incorporated herein by reference. Further alternatively or additionally, techniques described herein are practiced in conjunction with methods and apparatus described in U.S. Provisional Patent Application 60/383,157 to Ayal et al., filed May 23, 2002, entitled, "Inverse recruitment for autonomic nerve systems," which is assigned to the assignee of the present patent application and is incorporated herein by reference.

FIG. 2C is a simplified perspective illustration of electrode device 40 (FIG. 2A), in accordance with an embodiment of the present invention. When applied to vagus nerve 36, electrode device 40 typically encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes typically comprise ring electrodes adapted to apply a generally uniform current around the circumference of the nerve, as best shown in FIG. 2C.

FIG. 3 is a simplified perspective illustration of a multipolar point electrode device 140 applied to vagus nerve 36, in accordance with an embodiment of the present invention. In this embodiment, anodes 144a and 144b and a cathode 146 typically comprise point electrodes (typically 2 to 100), fixed inside an insulating cuff 148 and arranged around vagus nerve 36 so as to selectively stimulate nerve fibers according to their positions inside the nerve. In this case, techniques described in the above-cited articles by Grill et al., Goodall et al., and/or Veraart et al. are typically used. The point electrodes typically have a surface area between about 0.01 mm$^2$ and 1 mm$^2$. In some applications, the point electrodes are in contact with vagus nerve 36, as shown, while in other applications the point electrodes are recessed in cuff 148, so as not to come in direct contact with vagus nerve 36, similar to the recessed ring electrode arrangement described above with reference to FIG. 2A. For some applications, one or more of the electrodes, such as cathode 146 or anode 144a, comprise a ring electrode, as described with reference to FIG. 2C, such that electrode device 140 comprises both ring electrode(s) and point electrodes (configuration not shown). Additionally, electrode device 40 optionally comprises an afferent anode set (positioned like anodes 45a and 45b in FIG. 2A), the anodes of which comprise point electrodes and/or ring electrodes.

Alternatively, ordinary, non-cuff electrodes are used, such as when the electrodes are placed on the epicardial fat pads instead of on the vagus nerve.

Figure 4:
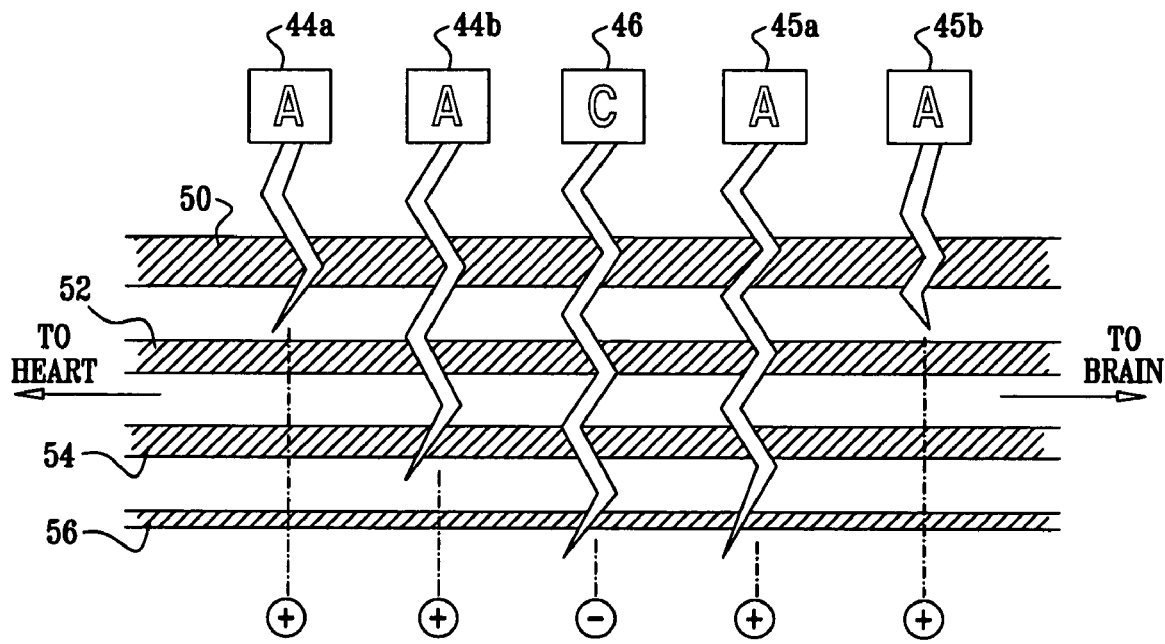
FIG. 4 is a conceptual illustration of the application of current to a vagus nerve, in accordance with an embodiment of the present invention.

FIG. 4 is a conceptual illustration of the application of current to vagus nerve 36 in order to achieve smaller-to-larger diameter fiber recruitment, in accordance with an embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 4 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 36.

In order to suppress artificially-induced afferent action potentials from traveling towards the brain in response to the cathodic stimulation, control unit 20 typically drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve.

For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

In an embodiment of the present invention, stimulation of the vagus nerve is applied responsive to one or more sensed parameters. Control unit 20 is typically configured to commence or halt stimulation, or to vary the amount and/or timing of stimulation in order to achieve a desired target heart rate, typically based on configuration values and on parameters including one or more of the following:

Heart rate—the control unit can be configured to drive electrode device 40 to stimulate the vagus nerve only when the heart rate exceeds a certain value.

ECG readings—the control unit can be configured to drive electrode device 40 to stimulate the vagus nerve based on certain ECG readings, such as readings indicative of designated forms of arrhythmia. Additionally, ECG readings are typically used for achieving a desire heart rate, as described below with reference to FIG. 5.

Blood pressure—the control unit can be configured to regulate the current applied by electrode device 40 to the vagus nerve when blood pressure exceeds a certain threshold or falls below a certain threshold.

Indicators of decreased cardiac contractility—these indicators include left ventricular pressure (LVP). When LVP and/or d(LVP)/dt exceeds a certain threshold or falls below a certain threshold, control unit 20 can drive electrode device 40 to regulate the current applied by electrode device 40 to the vagus nerve.

Motion of the patient—the control unit can be configured to interpret motion of the patient as an indicator of increased exertion by the patient, and appropriately reduce parasympathetic stimulation of the heart in order to allow the heart to naturally increase its rate.

Heart rate variability—the control unit can be configured to drive electrode device 40 to stimulate the vagus nerve based on heart rate variability, which is typically calculated based on certain ECG readings.

Norepinephrine concentration—the control unit can be configured to drive electrode device 40 to stimulate the vagus nerve based on norepinephrine concentration.

Cardiac output—the control unit can be configured to drive electrode device 40 to stimulate the vagus nerve based on cardiac output, which is typically determined using impedance cardiography.

Baroreflex sensitivity—the control unit can be configured to drive electrode device 40 to stimulate the vagus nerve based on baroreflex sensitivity.

The parameters and behaviors included in this list are for illustrative purposes only, and other possible parameters and/or behaviors will readily present themselves to those skilled in the art, having read the disclosure of the present patent application.

In an embodiment of the present invention, control unit 20 is configured to drive electrode device 40 to stimulate the vagus nerve so as to reduce the heart rate of the subject towards a target heart rate. The target heart rate is typically (a) programmable or configurable, (b) determined responsive to one or more sensed physiological values, such as those described hereinabove (e.g., motion, blood pressure, etc.), and/or (c) determined responsive to a time of day or circadian cycle of the subject. Parameters of stimulation are varied in real time in order to vary the heart-rate-lowering effects of the stimulation. For example, such parameters may include the amplitude of the applied current. Alternatively or additionally, in an embodiment of the present invention, the stimulation is applied in a series of pulses that are synchronized or are not synchronized with the cardiac cycle of the subject, such as described hereinbelow with reference to FIG. 5. Parameters of such pulse series typically include, but are not limited to:

Timing of the stimulation within the cardiac cycle. Delivery of the series of pulses typically begins after a fixed or variable delay following an ECG feature, such as each R- or P-wave. For some applications, the delay is between about 20 ms and about 300 ms from the R-wave, or between about 100 and about 500 ms from the P-wave.

Pulse duration (width). Longer pulse durations typically result in a greater heart-rate-lowering effect. For some applications, the pulse duration is between about 0.2 and about 4 ms.

Pulse repetition interval. Maintaining a pulse repetition interval (the time from the initiation of a pulse to the initiation of the following pulse) greater than about 3 ms generally results in maximal stimulation effectiveness for multiple pulses within a burst.

Pulses per trigger (PPT). A greater PPT (the number of pulses in each series of pulses after a trigger such as an R-wave) typically results in a greater heart-rate-lowering effect. For some applications, PPT is between about 0 and about 8.

Amplitude. A greater amplitude of the signal applied typically results in a greater heart-rate-lowering effect. The amplitude is typically less than about 10 milliamps, e.g., between about 2 and about 10 milliamps. For some applications, the amplitude is between about 2 and about 6 milliamps.

Duty cycle. Application of stimulation every heartbeat typically results in a greater heart-rate-lowering effect. For less heart rate reduction, stimulation is applied only once every several heartbeats.

Choice of vagus nerve. Stimulation of the right vagus nerve typically results in greater heart rate reduction than stimulation of the left vagus nerve.

"On"/"off" ratio and timing. For some applications, the device operates intermittently, alternating between "on" and "off" states, the length of each state typically between 0 and about 300 seconds (with a 0-length "off" state equivalent to always "on"). Greater heart rate reduction is typically achieved if the device is "on" a greater portion of the time.

For some applications, values of the "on"/"off" parameter are determined in real time, responsive to one or more inputs, such as sensed physiological values. Such inputs typically include motion or activity of the subject (e.g., detected using an accelerometer), the average heart rate of the subject when the device is in "off" mode, and/or the time of day. For example, the device may operate in continuous "on" mode when the subject is exercising and therefore has a high heart rate, and the device may alternate between "on" and "off" when the subject is at rest. As a result, the heart-rate-lowering effect is concentrated during periods of high heart rate, and the nerve is allowed to rest when the heart rate is generally naturally lower.

For some applications, heart rate regulation is achieved by setting two or more parameters in combination. For example, if it is desired to apply 5.2 pulses of stimulation, the control unit may apply 5 pulses of 1 ms duration each, followed by a single pulse of 0.2 ms duration. For other applications, the control unit switches between two values of PPT, so that the desired PPT is achieved by averaging the applied PPTs. For example, a sequence of PPTs may be 5, 5, 5, 5, 6, 5, 5, 5, 5, 6, . . . , in order to achieve an effective PPT of 5.2.

In an embodiment of the present invention, control unit 20 uses a slow-reacting heart rate regulation algorithm to modify heart-rate-controlling parameters of the stimulation, i.e., the algorithm varies stimulation parameters slowly in reaction to changes in heart rate. For example, in response to a sudden increase in heart rate, e.g., an increase from a target heart rate of 60 beats per minute (BPM) to 100 BPM over a period of only a few seconds, the algorithm slowly increases the stimulation level over a period of minutes. If the heart rate naturally returns to the target rate over this period, the stimulation levels generally do not change substantially before returning to baseline levels.

For example, the heart of a subject is regulated while the subject is inactive, such as while sitting. When the subject suddenly increases his activity level, such as by standing up or climbing stairs, the subject's heart rate increases suddenly. In response, the control unit adjusts the stimulation parameters slowly to reduce the subject's heart rate. Such a gradual modification of stimulation parameters allows the subject to engage in relatively stressful activities for a short period of time before his heart rate is substantially regulated, generally resulting in an improved quality of life.

In an embodiment of the present invention, control unit 20 is adapted to detect bradycardia (i.e., that an average detected R-R interval exceeds a preset bradycardia limit), and to terminate heart rate regulation substantially immediately upon such detection, such as by ceasing vagal stimulation. Alternatively or additionally, the control unit uses an algorithm that reacts quickly to regulate heart rate when the heart rate crosses limits that are predefined (e.g., a low limit of 40 beats per minute (BPM) and a high limit of 140 BPM), or determined in real time, such as responsive to sensed physiological values.

In an embodiment of the present invention, control unit 20 is configured to operate intermittently. Typically, upon each resumption of operation, control unit 20 sets the stimulation parameters to those in effect immediately prior to the most recent cessation of operation. For some applications, such parameters applied upon resumption of operation are maintained without adjustment for a certain number of heartbeats (e.g., between about one and about ten), in order to allow the heart rate to stabilize after resumption of operation.

For some applications, control unit 20 is configured to operate intermittently with gradual changes in stimulation. For example, the control unit may operate according to the following "on"/"off"pattern: (a) "off" mode for 30 minutes, (b) a two-minute "on" period characterized by a gradual increase in stimulation so as to achieve a target heart rate, (c) a six-minute "on" period of feedback-controlled stimulation to maintain the target heart rate, and (d) a two-minute "on" period characterized by a gradual decrease in stimulation to return the heart rate to baseline. The control unit then repeats the cycle, beginning with another 30-minute "off" period.

In an embodiment of the present invention, control unit 20 is configured to operate in an adaptive intermittent mode. The control unit sets the target heart rate for the "on" period equal to a fixed or configurable fraction of the average heart rate during the previous "off" period, typically bounded by a preset minimum. For example, assume that for a certain subject the average heart rates during sleep and during exercise are 70 and 150 BPM, respectively. Further assume that the target heart rate for the "on" period is set at 70% of the average heart rate during the previous "off" period, with a minimum of 60 BPM. During sleep, stimulation is applied so as to produce a heart rate of MAX(60 BPM, 70% of 70 BPM)=60 BPM, and is thus applied with parameters similar to those that would be used in the simple intermittent mode described hereinabove. Correspondingly, during exercise, stimulation is applied so as to produce a heart rate of MAX(60 BPM, 70% of 150 BPM)=105 BPM.

In an embodiment of the present invention, a heart rate regulation algorithm used by control unit 20 has as an input a time derivative of the sensed heart rate. The algorithm typically directs the control unit to respond slowly to increases in heart rate and quickly to decreases in heart rate.

In an embodiment of the present invention, the heart rate regulation algorithm utilizes sensed physiological parameters for feedback. For some applications, the feedback is updated periodically by inputting the current heart rate. For some applications, such updating occurs at equally-spaced intervals. Alternatively, the feedback is updated by inputting the current heart rate upon each detection of a feature of the ECG, such as an R-wave. In order to convert non-fixed R-R intervals into a form similar to canonical fixed intervals, the algorithm adds the square of each R-R interval, thus taking into account the non-uniformity of the update interval, e.g., in order to properly analyze feedback stability using standard tools and methods developed for canonical feedback.

In an embodiment of the present invention, control unit 20 implements a detection blanking period, during which the control unit does not detect heart beats. In some instances, such non-detection may reduce false detections of heart beats. One or both of the following techniques are typically implemented:

Absolute blanking. An expected maximal heart rate is used to determine a minimum interval between expected heart beats. During this interval, the control unit does not detect heart beats, thereby generally reducing false detections. For example, the expected maximal heart rate may be 200 BPM, resulting in a minimal detection interval of 300 milliseconds. After detection of a beat, the control unit disregards any signals indicative of a beat during the next 300 milliseconds.

Stimulation blanking. During application of a stimulation burst, and for an interval thereafter, the control unit does not detect heart beats, thereby generally reducing false detections of stimulation artifacts as beats.

For example, assume stimulation is applied with the following parameters: a PPT of 5 pulses, a pulse width of 1 ms, and a pulse repetition interval of 5 ms. The control unit disregards any signals indicative of a beat during the entire 25 ms duration of the burst and for an additional interval thereafter, e.g., 50 ms, resulting in a total blanking period of 75 ms beginning with the start of the burst.

In an embodiment of the present invention, the heart rate regulation algorithm is implemented using only integer arithmetic. For example, division is implemented as integer division by a power of two, and multiplication is always of two 8-bit numbers. For some applications, time is measured in units of $1/128$ of a second.

In an embodiment of the present invention, control unit 20 implements an integral feedback controller, which can most generally be described by:

$$K = K_I * \int e\, dt$$

in which K represents the strength of the feedback, $K_I$ is a coefficient, and $\int e\, dt$ represents the cumulative error. It is to be understood that such an integral feedback controller can be implemented in hardware, or in software running in control unit 20.

In an embodiment of such an integral controller, heart rate is typically expressed as an R-R interval (the inverse of heart rate). Parameters of the integral controller typically include TargetRR (the target R-R interval) and TimeCoeff (which determines the overall feedback reaction time).

Typically, following the detection of each R-wave, the previous R-R interval is calculated and assigned to a variable (LastRR). e (i.e., the difference between the target R-R interval and the last measured R-R interval) is then calculated as:

$$e = \text{TargetRR} - \text{LastRR}$$

e is typically limited by control unit 20 to a certain range, such as between −0.25 and +0.25 seconds, by reducing values outside the range to the endpoint values of the range. Similarly, LastRR is typically limited, such as to 255/128 seconds. The error is then calculated by multiplying LastRR by e:

$$\text{Error} = e * \text{LastRR}$$

A cumulative error (representing the integral in the above generalized equation) is then calculated by dividing the error by TimeCoeff and adding the result to the cumulative error, as follows:

$$\text{Integral} = \text{Integral} + \text{Error}/2^{\text{TimeCoeff}}$$

The integral is limited to positive values less than, e.g., 36,863. The number of pulses applied in the next series of pulses (pulses per trigger, or PPT) is equal to the integral/4096.

The following table illustrates example calculations using a heart rate regulation algorithm that implements an integral controller, in accordance with an embodiment of the present invention. In this example, the parameter TargetRR (the target heart rate) is set to 1 second ($128/128$ seconds), and the parameter TimeCoeff is set to 0. The initial value of Integral is 0. As can be seen in the table, the number of pulses per trigger (PPT) increases from 0 during the first heart beat, to 2 during the fourth heart beat of the example.

|  | Heart Beat Number | | | |
| --- | --- | --- | --- | --- |
|  | 1 | 2 | 3 | 4 |
| Heart rate (BPM) | 100 | 98 | 96 | 102 |
| R—R interval (ms) | 600 | 610 | 620 | 590 |
| R—R ($1/128$ sec) | 76 | 78 | 79 | 75 |
| e ($1/128$ sec) | 52 | 50 | 49 | 53 |
| Limited e | 32 | 32 | 32 | 32 |
| Error | 2432 | 2496 | 2528 | 2400 |
| Integral | 2432 | 4928 | 7456 | 9856 |
| PPT | 0 | 1 | 1 | 2 |

In an embodiment of the present invention, the heart rate regulation algorithm corrects for missed heart beats (either of physiological origin or because of a failure to detect a beat). Typically, to perform this correction, any R-R interval which is about twice as long as the immediately preceding R-R interval is interpreted as two R-R intervals, each having a length equal to half the measured interval. For example, the R-R interval sequence (measured in seconds) 1, 1, 1, 2.2 is interpreted by the algorithm as the sequence 1, 1, 1, 1.1, 1.1. Alternatively or additionally, the algorithm corrects for premature beats, typically by adjusting the timing of beats that do not occur approximately halfway between the preceding and following beats. For example, the R-R interval sequence (measured in seconds) 1, 1, 0.5, 1.5 is interpreted as 1, 1, 1, 1, using the assumption that the third beat was premature.

In an embodiment of the present invention, control unit 20 is configured to operate in one of the following modes:

vagal stimulation is not applied when the heart rate of the subject is lower than the low end of the normal range of a heart rate of the subject and/or of a typical human subject;

vagal stimulation is not applied when the heart rate of the subject is lower than a threshold value equal to the current low end of the range of the heart rate of the subject, i.e., the threshold value is variable over time as the low end generally decreases as a result of chronic vagal stimulation treatment;

vagal stimulation is applied only when the heart rate of the subject is within the normal of range of a heart rate of the subject and/or of a typical human subjects;

vagal stimulation is applied only when the heart rate of the subject is greater than a programmable threshold value, such as a rate higher than a normal rate of the subject and/or a normal rate of a typical human subject. This mode generally removes peaks in heart rate; or vagal stimulation is applied using fixed programmable parameters, i.e., not in response to any feedback, target heart rate, or target heart rate range. These parameters may be externally updated from time to time, for example by a physician.

In an embodiment of the present invention, the amplitude of the applied stimulation current is calibrated by fixing a number of pulses in the series of pulses (per cardiac cycle), and then increasing the applied current until a desired predetermined heart rate reduction is achieved. Alternatively, the current is calibrated by fixing the number of pulses per series of pulses, and then increasing the current to achieve a substantial reduction in heart rate, e.g., 40%.

In embodiments of the present invention in which vagal stimulation system 18 comprises implanted device 25 for monitoring and correcting the heart rate, control unit 20 typically uses measured parameters received from device 25 as additional inputs for determining the level and/or type of stimulation to apply. Control unit 20 typically coordinates its behavior with the behavior of device 25. Control unit 20 and device 25 typically share sensors 26 in order to avoid redundancy in the combined system.

Optionally, vagal stimulation system 18 comprises a patient override, such as a switch that can be activated by the patient using an external magnet. The override typically can be used by the patient to activate vagal stimulation, for example in the event of arrhythmia apparently undetected by the system, or to deactivate vagal stimulation, for example in the event of apparently undetected physical exertion.

Figure 5:
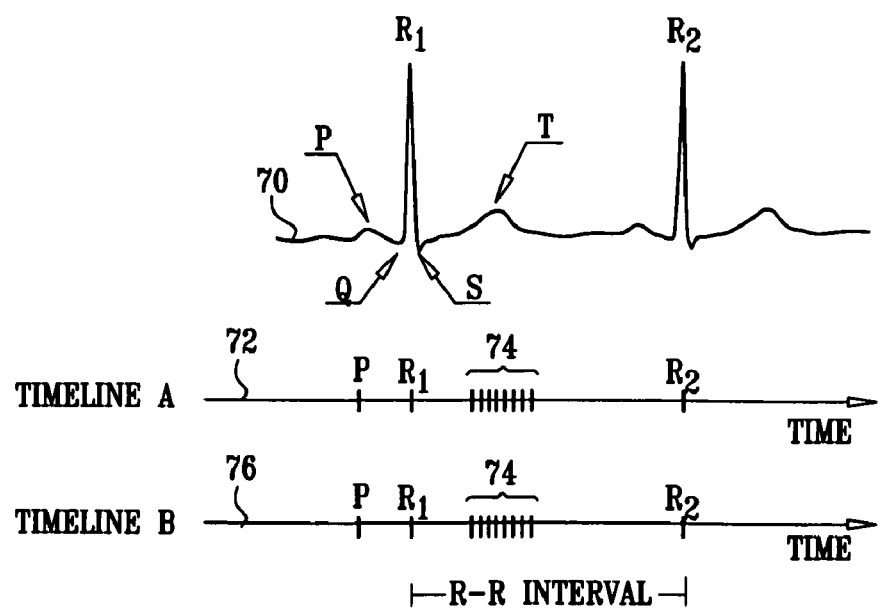
FIG. 5 is a simplified illustration of an electrocardiogram (ECG) recording and of example timelines showing the timing of the application of a series of stimulation pulses, in accordance with an embodiment of the present invention.

FIG. 5 is a simplified illustration of an ECG recording 70 and example timelines 72 and 76 showing the timing of the application of a burst of stimulation pulses 74, in accordance with an embodiment of the present invention. Stimulation is typically applied to vagus nerve 36 in a closed-loop system in order to achieve and maintain the desired target heart rate, determined as described above. Precise graded slowing of the heart beat is typically achieved by varying the number of nerve fibers stimulated, in a smaller-to-larger diameter order, and/or the intensity of vagus nerve stimulation, such as by changing the stimulation amplitude, pulse width, PPT, and/or delay. Stimulation with blocking, as described herein, is typically applied during each cardiac cycle in burst of pulses 74, typically containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

In an embodiment of the present invention (e.g., when the heart rate regulation algorithm described hereinabove is not implemented), to apply the closed-loop system, the target heart rate is expressed as a ventricular R-R interval (shown as the interval between $R_1$ and $R_2$ in FIG. 5). The actual R-R interval is measured in real time and compared with the target R-R interval. The difference between the two intervals is defined as a control error. Control unit 20 calculates the change in stimulation necessary to move the actual R-R towards the target R-R, and drives electrode device 40 to apply the new calculated stimulation. Intermittently, e.g., every 1, 10, or 100 beats, measured R-R intervals or average R-R intervals are evaluated, and stimulation of the vagus nerve is modified accordingly.

In an embodiment, vagal stimulation system 18 is further configured to apply stimulation responsive to pre-set time parameters, such as intermittently, constantly, or based on the time of day.

Alternatively or additionally, one or more of the techniques of smaller-to-larger diameter fiber recruitment, selective fiber population stimulation and blocking, and varying the intensity of vagus nerve stimulation by changing the stimulation amplitude, pulse width, PPT, and/or delay, are applied in conjunction with methods and apparatus described in one or more of the patents, patent applications, articles and books cited herein.

In an embodiment of the present invention, control unit 20 is configured to stimulate vagus nerve 36 so as to suppress the adrenergic system, in order to treat a subject suffering from a heart condition. For example, such vagal stimulation may be applied for treating a subject suffering from heart failure. In heart failure, hyper-activation of the adrenergic system damages the heart. This damage causes further activation of the adrenergic system, resulting in a vicious cycle. High adrenergic tone is harmful because it often results in excessive release of angiotensin and epinephrine, which increase vascular resistance (blood pressure), reduce heart rest time (accelerated heart rate), and cause direct toxic damage to myocardial muscles through oxygen free radicals and DNA damage. Artificial stimulation of the vagus nerve causes a down regulation of the adrenergic system, with reduced release of catecholamines. The natural effects of vagal stimulation, applied using the techniques described herein, typically reduces the release of catecholamines in the heart, thereby lowering the adrenergic tone at its source.

In an embodiment of the present invention, control unit 20 is configured to stimulate vagus nerve 36 so as to modulate atrial and ventricular contractility, in order to treat a subject suffering from a heart condition. Vagal stimulation generally reduces both atrial and ventricular contractility (see, for example, the above-cited article by Levy M N et al., entitled "Parasympathetic Control of the Heart"). Vagal stimulation, using the techniques described herein, typically (a) reduces the contractility of the atria, thereby reducing the pressure in the venous system, and (b) reduces the ventricular contractile force of the atria, which may reduce oxygen consumption, such as in cases of ischemia. For some applications, vagal stimulation, as described herein, is applied in order to reduce the contractile force of the ventricles in cases of hypertrophic cardiopathy. The vagal stimulation is typically applied with a current of at least about 4 mA.

In an embodiment of the present invention, control unit 20 is configured to stimulate vagus nerve 36 so as to improve coronary blood flow, in order to treat a subject suffering from a heart condition. Improving coronary blood flow by administering acetylcholine is a well known technique. For example, during Percutaneous Transluminal Coronary Angioplasty (PTCA), when maximal coronary dilation is needed, direct infusion of acetylcholine is often used to dilate the coronary arteries (see, for example, the above-cited article by Feliciano L et al.). For some applications, the vagal stimulation techniques described herein are used to improve coronary blood flow in subjects suffering from myocardial ischemia, ischemic heart disease, heart failure, and/or variant angina (spastic coronary arteries). It is hypothesized that such vagal stimulation simulates the effect of acetylcholine administration.

In an embodiment of the present invention, control unit 20 is configured to drive electrode device 40 to stimulate vagus nerve 36 so as to modify heart rate variability of the subject. For some applications, control unit 20 is configured to apply the stimulation having a duty cycle, which typically produces heart rate variability at the corresponding frequency. For example, such duty cycles may be in the range of once per every several heartbeats. For other applications, control unit 20 is configured to apply generally continuous stimulation (e.g., in a manner that produces a prolonged reduced level of heart rate variability).

For some applications, control unit 20 synchronizes the stimulation with the cardiac cycle of the subject, while for other applications, the control unit does not synchronize the stimulation with the cardiac cycle. For example, the stimulation may be applied in a series of pulses that are not synchronized with the cardiac cycle of the subject. Alternatively, the stimulation may be applied in a series of pulses that are synchronized with the cardiac cycle of the subject, such as described hereinabove with reference to FIG. 5.

For some applications, control unit 20 is configured to apply stimulation with parameters selected to reduce heart rate variability, while for other applications parameters are selected that increase variability. For example, when the stimulation is applied as a series of pulses, values of parameters that reduce heart variability may include one or more of the following:

Timing of the stimulation within the cardiac cycle: a delay of between about 50 ms and about 150 ms from the R-wave, or between about 100 and about 500 ms from the P-wave.

Pulse duration (width) of between about 0.5 and about 1.5 ms.

Pulse repetition interval (the time from the initiation of a pulse to the initiation of the following pulse) of between about 2 and about 8 ms.

Pulses per trigger (PPT), e.g., pulses per cardiac cycle, of between about 0 and about 8.

Amplitude of between about 5 and about 10 milliamps.

For some applications, the parameters of the stimulation are selected to both reduce the heart rate of the subject and heart rate variability of the subject. For other applications, the parameters are selected to reduce heart rate variability while substantially not reducing the average heart rate of the subject. In this context, a non-substantial heart rate reduction may be less than about 10%. For some applications, to achieve such a reduction in variability without a reduction in average rate, stimulation is applied using the feedback techniques described hereinabove, with a target heart rate greater than the normal average heart rate of the subject. Such stimulation typically does not substantially change the average heart rate, yet reduces heart rate variability (however, the instantaneous (but not average) heart rate may sometimes be reduced).

For some applications, in order to additionally reduce the heart rate, stimulation is applied using a target heart rate lower than the normal average heart rate of the subject. The magnitude of the change in average heart rate as well as the percentage of time during which reduced heart rate variability occurs in these applications are controlled by varying the difference between the target heart rate and the normal average heart rate.

For some applications, control unit 20 is configured to apply stimulation only when the subject is awake. Reducing heart variability when the subject is awake offsets natural increases in heart rate variability during this phase of the circadian cycle. Alternatively or additionally, control unit 20 is configured to apply or apply greater stimulation at times of exertion by the subject, in order to offset the increase in heart rate variability typically caused by exertion. For example, control unit 20 may determine that the subject is experiencing exertion responsive to an increase in heart rate, or responsive to a signal generated by an accelerometer. Alternatively, the control unit uses other techniques known in the art for detecting exertion.

In an embodiment of the present invention, control unit 20 is configured to drive electrode device 40 to stimulate vagus nerve 36 so as to modify heart rate variability in order to treat a condition of the subject. For some applications, the control unit is configured to additionally modify heart rate to treat the condition, while for other applications, the control unit is configured to modify heart rate variability while substantially not modifying average heart rate.

Therapeutic effects of reduction in heart rate variability include, but are not limited to:

Narrowing of the heart rate range, thereby eliminating very slow heart rates and very fast heart rates, both of which are inefficient for a subject suffering from heart failure. For this therapeutic application, control unit 20 is typically configured to reduce low-frequency heart rate variability, and to adjust the level of stimulation applied based on the circadian and activity cycles of the subject.

Stabilizing the heart rate, thereby reducing the occurrence of arrhythmia. For this therapeutic application, control unit 20 is typically configured to reduce heart rate variability at all frequencies.

Maximizing the mechanical efficiency of the heart by maintaining relatively constant ventricular filling times and pressures. For example, this therapeutic effect may be beneficial for subjects suffering from atrial fibrillation, in which fluctuations in heart filling times and pressure reduce cardiac efficiency.

Eliminating the normal cardiac response to changes in the breathing cycle (i.e., respiratory sinus arrhythmia). Although generally beneficial in young and efficient hearts, respiratory sinus arrhythmia may be harmful to subjects suffering from heart failure, because respiratory sinus arrhythmia causes unwanted accelerations and decelerations in the heart rate. For this therapeutic application, control unit 20 is typically configured to reduce heart rate variability at high frequencies.

Figure 6:
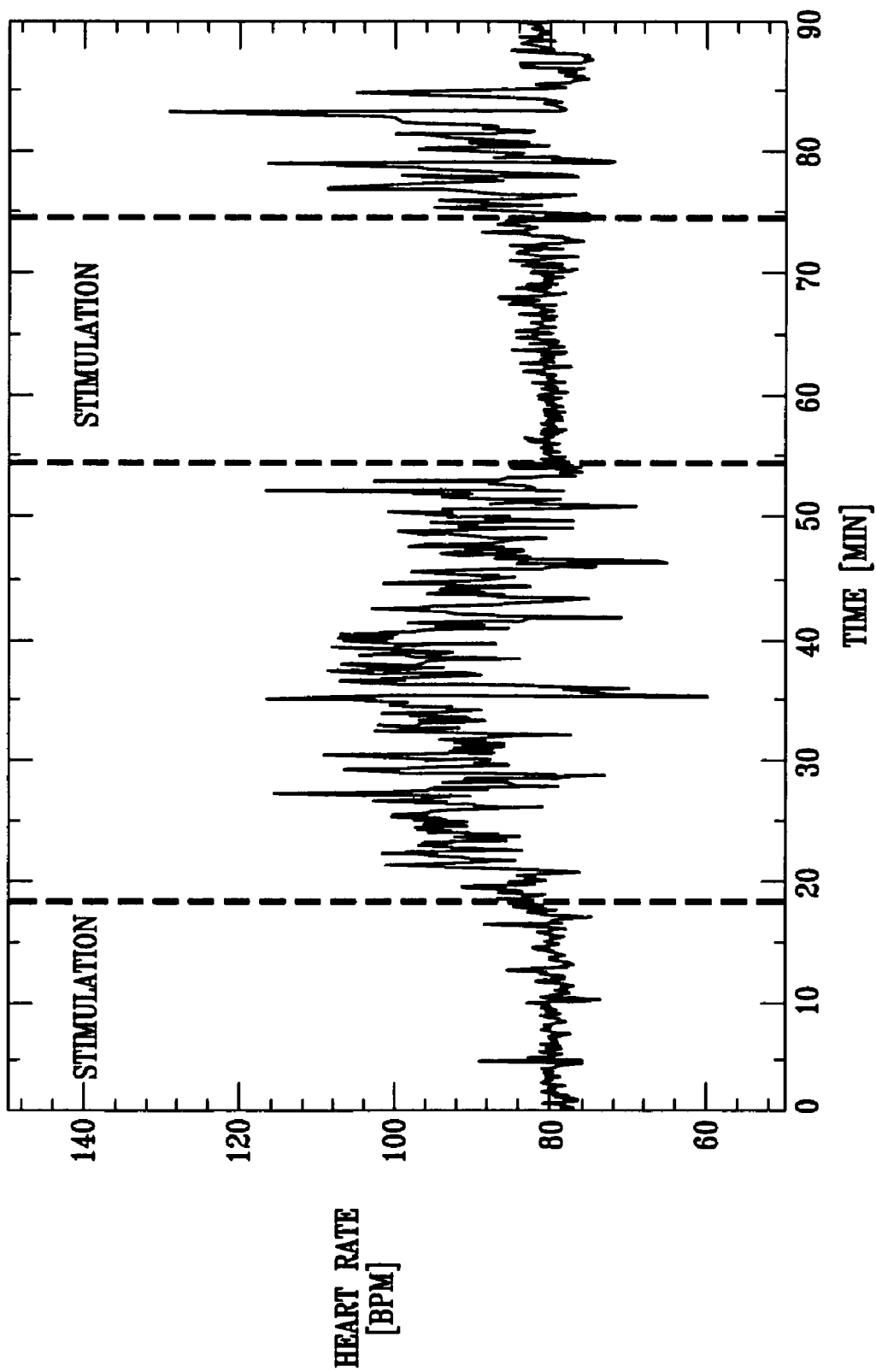
FIG. 6 is a graph showing in vivo experimental results, measured in accordance with an embodiment of the present invention.

Reference is now made to FIG. 6, which is a graph showing in vivo experimental results, measured in accordance with an embodiment of the present invention. A dog was anesthetized, and cuff electrodes, similar to those described hereinabove with reference to FIG. 2B, were implanted in the right cervical vagus nerve. After a recovery period of two weeks, experimental vagal stimulation was applied to the dog while the dog was awake and allowed to move freely within its cage.

A control unit, similar to control unit 20, was programmed to apply vagal stimulation in a series of pulses, having the following parameters:

Stimulation synchronized with the intracardiac R-wave signal, with a delay from the R-wave of 60 ms;

Stimulation amplitude of 8 mA;

Stimulation pulse duration of 1 ms; and

Time between pulses within a burst of 5 ms.

The control unit implemented an integral feedback controller, similar to the integral feedback controller described hereinabove, in order to vary the number of pulses within a burst. The integral feedback controller used a target heart rate of 80 beats per minute. After 2 minutes of stimulation, the number of pulses within each burst was typically between about 1 and about 8.

During a first period and a third period from 0 to 18 minutes and 54 to 74 minutes, respectively, the control unit applied stimulation to the vagus nerve. Heart rate variability was substantially reduced, while an average heart rate of 80 beats per minute was maintained. (Baseline heart rate, without stimulation, was approximately 95 beats per minute.) During a second period and a fourth period from 18 to 54 minutes and 74 to 90 minutes, respectively, stimulation was discontinued, and, as a result, heart rate variability increased substantially, returning to normal values. Average heart rate during these non-stimulation periods increased to approximately 95 beats per minute (approximately baseline value). Thus, these experimental results demonstrate that the application of vagal stimulation using some of the techniques described herein results in a substantial reduction in heart rate variability.

Although embodiments of the present invention are described herein, in some cases, with respect to treating specific heart conditions, it is to be understood that the scope of the present invention generally includes utilizing the techniques described herein to controllably stimulate the vagus nerve to facilitate treatments of, for example, heart failure, atrial fibrillation, and ischemic heart diseases. In particular, the techniques described herein may be performed in combination with other techniques, which are well known in the art or which are described in the references cited herein, that stimulate the vagus nerve in order to achieve a desired therapeutic end.

For some applications, techniques described herein are used to apply controlled stimulation to one or more of the following: the lacrimal nerve, the salivary nerve, the vagus nerve, the pelvic splanchnic nerve, or one or more sympathetic or parasympathetic autonomic nerves. Such controlled stimulation may be used, for example, to regulate or treat a condition of the lung, heart, stomach, pancreas, small intestine, liver, spleen, kidney, bladder, rectum, large intestine, reproductive organs, or adrenal gland.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a subject, comprising:
   identifying that the subject suffers from heart failure; and
   treating the heart failure by:
   determining that a heart rate of the subject is within a normal heart-rate range of the subject; and
   responsively to the determination, applying, only when the heart rate is within the normal heart-rate range of the subject, a current to a site of the subject selected from the group consisting of: a vagus nerve and an epicardial fat pad.

2. The method according to claim 1, wherein applying the current comprises:
   applying current in respective pulse bursts in each of a plurality of cardiac cycles of the subject; and
   synchronizing the bursts with the cardiac cycles.

3. The method according to claim 2, wherein applying the current comprises setting a control parameter of a feedback algorithm governing the current application to be a number of pulses per each one of the bursts.

4. The method according to claim 3, wherein the feedback algorithm includes an integral feedback algorithm that has inputs including the heart rate of the subject and the threshold value.

5. The method according to claim 1, wherein applying the current comprises cycling between "on" periods, during which the current is applied, and "off" periods, during which the current is withheld.

6. The method according to claim 1, wherein applying the current comprises configuring the current using fixed programmable parameters that do not vary in response to any feedback.

* * * * *